(12) United States Patent
Cerny et al.

(10) Patent No.: US 9,984,209 B2
(45) Date of Patent: May 29, 2018

(54) GRAPHICAL CONTROLS FOR PROGRAMMING MEDICAL DEVICE OPERATION

(71) Applicant: Medtronic, Inc., Minneapolis, MN (US)

(72) Inventors: Douglas S. Cerny, Minneapolis, MN (US); Timmothy S. Carlson, Fridley, MN (US); Raj Mehra, Savage, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days. days.

(21) Appl. No.: 15/044,825

(22) Filed: Feb. 16, 2016

(65) Prior Publication Data

US 2016/0246935 A1    Aug. 25, 2016

Related U.S. Application Data

(60) Provisional application No. 62/115,825, filed on Feb. 13, 2015.

(51) Int. Cl.
*A61N 1/372* (2006.01)
*G06F 19/00* (2018.01)
(Continued)

(52) U.S. Cl.
CPC ......... *G06F 19/3406* (2013.01); *A61M 5/142* (2013.01); *A61M 5/172* (2013.01);
(Continued)

(58) Field of Classification Search
CPC ............ A61N 1/37235; A61N 1/37247; G06F 3/0484; G06F 3/04847
(Continued)

(56) References Cited

U.S. PATENT DOCUMENTS 5,983,140 A    11/1999    Smith et al.
6,034,688 A     3/2000    Greenwood et al.
(Continued)

FOREIGN PATENT DOCUMENTS

| EP | 0773038 B1 | 2/2004 |
|----|------------|--------|
| WO | 2001083028 A1 | 11/2001 |
| WO | 2004041351 A1 | 5/2004 |

OTHER PUBLICATIONS

"Identifying iPod models," http://support.apple.com/kb/HT1353#iPod_classic_160GB, archived on Mar. 20, 2009, last modified Feb. 4, 2009, at http://web.archive.org, 11 pp.

*Primary Examiner* — Allen Porter, Jr.
(74) *Attorney, Agent, or Firm* — Shumaker & Sieffert, P.A.

(57) ABSTRACT

An example method includes presenting, by a computing device, a range of available parameter values for the therapy parameter via a circular track, indicating, by the computing device, a present parameter value for the therapy parameter via the circular track, and receiving, by the computing device, via a user interface (UI), user input specifying a target parameter value for the therapy parameter, indicating, by the computing device, the target parameter value in conjunction with the present parameter value via the circular track, receiving by the computing device, via the UI, user input activating an adjustment from the present parameter value to the target parameter value, and in response to receiving the user input activating the adjustment, controlling, by the computing device, the medical device to adjust the therapy parameter value from the present parameter value to the target parameter value.

30 Claims, 15 Drawing Sheets

(51) Int. Cl.
*A61N 1/05* (2006.01)
*A61M 5/172* (2006.01)
*A61M 5/142* (2006.01)

(52) U.S. Cl.
CPC ......... *A61N 1/0534* (2013.01); *A61N 1/0551* (2013.01); *A61N 1/37247* (2013.01); *A61M 2205/502* (2013.01)

(58) Field of Classification Search
USPC ................................................ 715/833, 834
See application file for complete search history.

(56) References Cited

U.S. PATENT DOCUMENTS

| | | | |
|---|---|---|---|
| 6,052,624 A | 4/2000 | Mann | |
| 6,106,464 A | 8/2000 | Bass et al. | |
| 6,229,456 B1 | 5/2001 | Engholm et al. | |
| 6,451,015 B1 | 9/2002 | Rittman et al. | |
| 6,992,658 B2 | 1/2006 | Wu et al. | |
| 7,033,326 B1 | 4/2006 | Pianca et al. | |
| 7,035,691 B2 | 4/2006 | Campos | |
| 7,602,382 B2 | 10/2009 | Hinckley et al. | |
| 7,646,378 B2 | 1/2010 | Hirshberg | |
| 8,121,694 B2 | 2/2012 | Molnar et al. | |
| 8,175,720 B2 | 5/2012 | Skelton et al. | |
| 8,249,717 B2 | 8/2012 | Brockway et al. | |
| 8,255,060 B2 | 8/2012 | Goetz et al. | |
| 8,588,929 B2 | 11/2013 | Skelton et al. | |
| 8,694,118 B2 | 4/2014 | Armstrong | |
| 8,831,731 B2 | 9/2014 | Blum et al. | |
| 8,843,209 B2 | 9/2014 | Wacnik et al. | |
| 8,886,302 B2 | 11/2014 | Skelton et al. | |
| 8,918,184 B1 | 12/2014 | Torgerson et al. | |
| 2005/0070781 A1 | 3/2005 | Dawant et al. | |
| 2006/0017749 A1 | 1/2006 | McIntyre et al. | |
| 2006/0092177 A1 | 5/2006 | Blasko | |
| 2006/0094951 A1 | 5/2006 | Dean et al. | |
| 2006/0229687 A1 | 10/2006 | Goetz et al. | |
| 2006/0259099 A1 | 11/2006 | Goetz et al. | |
| 2007/0203544 A1 | 8/2007 | Goetz et al. | |
| 2008/0154340 A1 | 6/2008 | Goetz et al. | |
| 2008/0163097 A1 | 7/2008 | Goetz et al. | |
| 2008/0211784 A1 | 9/2008 | Hotelling et al. | |
| 2009/0167704 A1 | 7/2009 | Terlizzi et al. | |
| 2009/0281596 A1 | 11/2009 | King et al. | |
| 2010/0010566 A1 | 1/2010 | Thacker et al. | |
| 2010/0207911 A1 | 8/2010 | Newton | |
| 2011/0115734 A1 | 5/2011 | Harashima et al. | |
| 2011/0270358 A1 | 11/2011 | Davis et al. | |
| 2013/0249814 A1 | 9/2013 | Zeng | |
| 2014/0052033 A1 | 2/2014 | Lawlis et al. | |
| 2014/0121555 A1 | 5/2014 | Scott et al. | |
| 2014/0277262 A1 | 9/2014 | Rao et al. | |
| 2014/0277284 A1 | 9/2014 | Chen et al. | |
| 2014/0350635 A1 | 11/2014 | Strother et al. | |
| 2014/0359508 A1 | 12/2014 | Otero et al. | |

GRAPHICAL CONTROLS FOR PROGRAMMING MEDICAL DEVICE OPERATION

This application claims the benefit of U.S. Provisional Application No. 62/115,825, filed on 13 Feb. 2015, the entire contents of which are incorporated herein by reference.

TECHNICAL FIELD

The disclosure relates to control of medical device operation by adjusting parameters via a programmer.

BACKGROUND

Implantable medical devices such as electrical stimulators or fluid delivery pumps, may be used to deliver therapy to patients to alleviate any of a variety of symptoms or conditions. Electrical stimulators, for example, may be used to deliver electrical stimulation therapy to patients to treat a variety of symptoms or conditions such as chronic pain, tremor, Parkinson's disease, epilepsy, urinary or fecal incontinence, sexual dysfunction, obesity, or gastroparesis. In general, an implantable stimulator may deliver stimulation therapy (e.g., neurostimulation therapy) in the form of electrical pulses or continuous waveforms. An implantable stimulator may deliver stimulation therapy via one or more leads that include electrodes located proximate to target locations associated with the brain, the spinal cord, pelvic nerves, peripheral nerves, or the gastrointestinal tract of a patient. Hence, stimulation may be used in different therapeutic applications, such as deep brain stimulation (DBS), spinal cord stimulation (SC S), pelvic stimulation, gastric stimulation, or peripheral nerve stimulation. Stimulation also may be used for muscle stimulation, e.g., functional electrical stimulation (FES), to promote muscle movement or prevent atrophy.

In general, a clinician selects values for a number of stimulation parameters in order to define the electrical stimulation therapy to be delivered by the implantable stimulator. For example, the clinician may select stimulation parameters that define a current or voltage amplitude of electrical pulses delivered by the stimulator, a pulse rate, a pulse width, and a configuration of electrodes that deliver the pulses, e.g., in terms of selected electrodes and associated polarities. The stimulation parameters selected by the clinician may be referred to as a "stimulation program." In some cases, therapy corresponding to multiple programs may be delivered on an alternating or continuous basis, as a group of programs.

SUMMARY

In general, the disclosure is directed to devices, systems, and techniques for adjusting parameters, such as numerical values, states, or identification information, used as parameters for control of the operation of a medical device. Aspects of this disclosure are directed to providing a graphical user interface (UI)-based control element (e.g., a circular adjustment control element) that enables a user to change states, values, identifiers, and various other parameters for operation of a medical device, such as an electrical stimulator. For instance, the circular adjustment control element may enable a user, such as a clinician, to perform circular motions with a finger, e.g., on or proximate to a touch screen of a programming device, to change the parameters applied by the medical device.

In some examples, a circular adjustment control element may enable a user to set a desired value for a parameter, and to leverage various computing modules (such as a hardware system implementing software) to move the parameter to one or more desired values in discrete steps. Adjustment of the parameter in discrete steps may potentially mitigate or prevent discomfort for a patient in the process of parameters being adjusted. For instance, aspects of this disclosure may alleviate discomfort and/or pain while a clinician adjusts therapy parameters to adjust the patient's therapy. To keep the clinician aware of a current state/value and a desired state/value, the circular adjustment control element may display an indication of where the present state/value is, relative to the desired state/value during adjustment in discrete steps.

In some examples, this disclosure is directed to a method for adjusting a therapy parameter for a medical device. The method includes presenting, by a computing device a range of available parameter values for the therapy parameter via a circular track, indicating, by the computing device, a present parameter value for the therapy parameter via the circular track, and receiving, by the computing device, via a user interface (UI), user input specifying a target parameter value for the therapy parameter. The method further includes indicating, by the computing device, the target parameter value in conjunction with the present parameter value via the circular track, receiving by the computing device, via the UI, user input activating an adjustment from the present parameter value to the target parameter value, and in response to receiving the user input activating the adjustment, controlling, by the computing device, the medical device to adjust the therapy parameter value from the present parameter value to the target parameter value.

In some examples, this disclosure is directed to a programming device for a medical device. The programming device includes a communication module configured to communicate with the medical device, a memory, a user interface (UI) configured to receive inputs and to output data via a circular track, and one or more processors. The processor(s) of the programming device are configured to present a range of available parameter values for the therapy parameter via a circular track, to indicate a present parameter value for the therapy parameter via the circular track, and to receive, via the UI, user input specifying a target parameter value for the therapy parameter. The processor(s) of the programming device are further configured to indicate the target parameter value in conjunction with the present parameter value via the circular track, to receive, via the UI, user input activating an adjustment from the present parameter value to the target parameter value and to control, in response to receiving the user input activating the adjustment, the medical device to adjust the therapy parameter value from the present parameter value to the target parameter value.

In some examples, this disclosure is directed to a system. The system includes a medical device and a programming device configured to communicate with the medical device. The programming device comprising one or more processors. The one or more processors of the programming device are configured to present a range of available parameter values for the therapy parameter via a circular track, to indicate a present parameter value for the therapy parameter via the circular track, and to receive, via a user interface (UI), user input specifying a target parameter value for the therapy parameter. The processor(s) of the programming device are further configured to indicate the target parameter value in conjunction with the present parameter value via the circular track, to receive, via the UI, user input activating an adjustment from the present parameter value to the target parameter value, and to control, in response to receiving the user input activating the adjustment, control the medical device to adjust the therapy parameter value from the present parameter value to the target parameter value.

Details of one or more examples are set forth in the accompanying drawings and the description below. Other features, objects, and advantages will be apparent from the description and drawings, and from the claims.

DETAILED DESCRIPTION

This disclosure is generally directed to devices, systems, and techniques for enabling a clinician (e.g., doctor, nurse, or other healthcare professional) to adjust parameters for controlling the operation of a medical device, such as an implantable medical device (IMD). Various aspects of this disclosure are directed to systems in which a clinician can adjust therapy parameters by operating a graphical control via an interactive user interface (UI). In various examples, this disclosure is directed to techniques for providing a circular control element via the interactive UI.

In some examples, the techniques may enable a clinician to adjust the parameters by moving an element (referred to herein as a "knob") around a circular track forming part of the circular control element. According to various aspects of this disclosure, the circular control element may be interactive in that the circular control element may display the present parameter level/state and the desired parameter level/state, as input by the clinician. In some examples, the parameter level/state may automatically be incrementally changed from the present value to the desired value, and the control element may display progress toward the desired value. In some examples, the UI-based circular control element of this disclosure may be implemented via a patient controller. Example use cases with respect to a patient controller-based implementation may include enabling a user to indicate a pain score (e.g., on a scale of one to ten) or to indicate an amount of time to turn off, deactivate, or suspend stimulation (e.g., with a provision to restart stimulation after 8 hours to aid the patient in sleeping).

Figure 1:
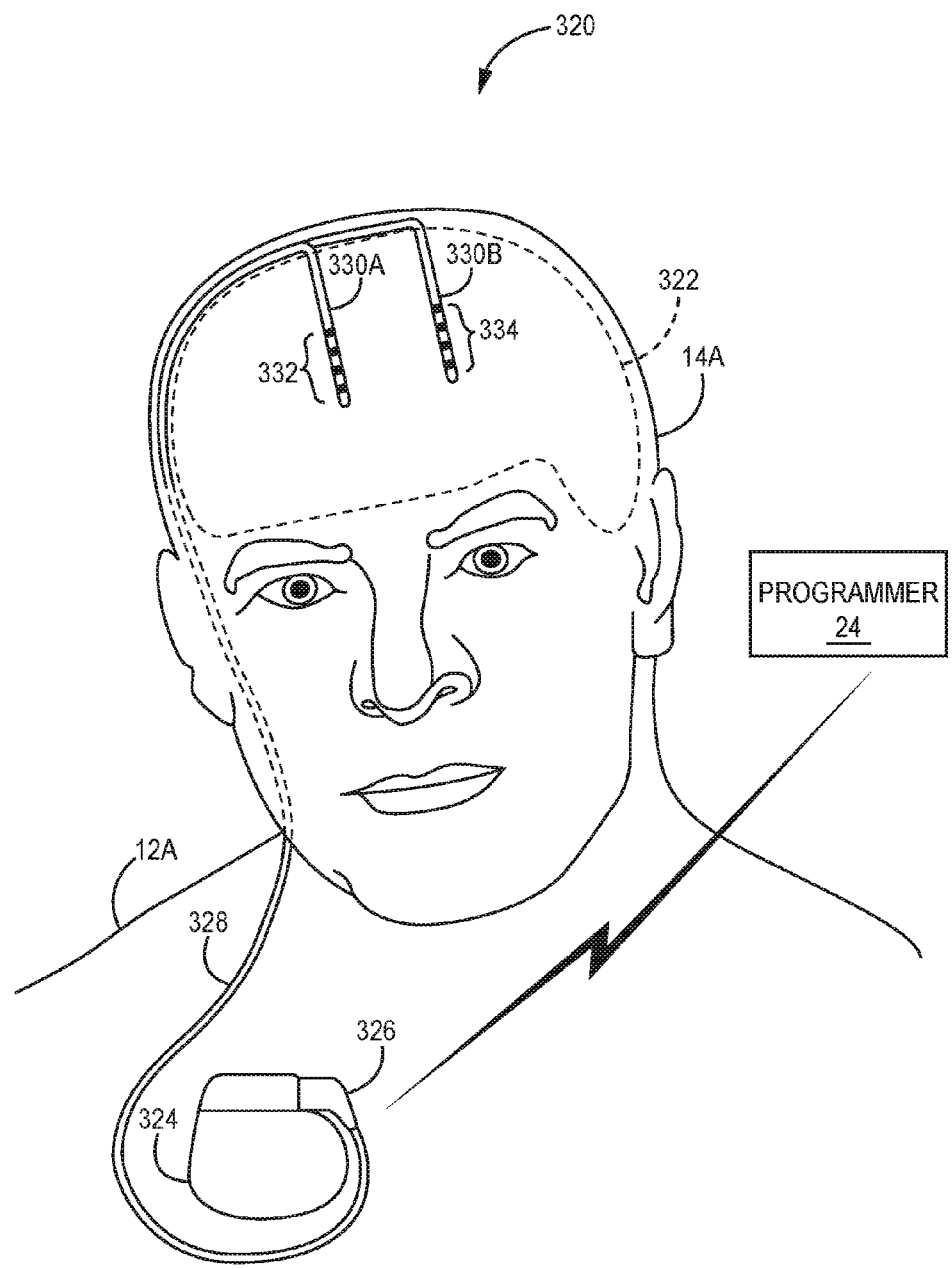
FIG. 1 is a conceptual diagram illustrating an example system that includes an implantable medical device (IMD) configured to deliver deep brain stimulation (DBS) to a patient and/or to sense one or more physiological signals of a patient.

FIG. 1 is a conceptual diagram illustrating example system 320 that includes implantable medical device (IMD) 324 configured to deliver deep brain stimulation (DBS) to patient 12A. Patient 12A may be patient 12A of FIGS. 1 and 2 or a different patient. Although the particular example of FIG. 1 is described herein with respect to DBS, aspects of this disclosure may be applicable to other types of electrical stimulation, such as spinal cord stimulation, pelvic floor stimulation, gastric stimulation, cardiac stimulation and various others. Aspects of this disclosure also may be applicable to other types of medical devices, such as external or implantable fluid delivery devices, e.g., for delivery of drugs, insulin, or other fluids. In the example of FIG. 1, for deep brain stimulation (DBS), system 320 may be configured to treat a patient condition, such as a movement disorder, neurodegenerative impairment, a mood disorder or a seizure disorder of patient 12A. Patient 12A ordinarily will be a human patient. In some cases, however, therapy system 320 may be applied to other mammalian or non-mammalian, non-human patients.

While movement disorders and neurodegenerative impairment are primarily referred to herein, in other examples, therapy system 320 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post-traumatic stress disorder, dysthymic disorder, and obsessive-compulsive disorder (OCD)). At least some of these disorders may be manifested in one or more patient movement behaviors. A movement disorder or other neurodegenerative impairment may include symptoms such as, for example, muscle control impairment, motion impairment or other movement problems, such as rigidity, spasticity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions.

Example therapy system 320 includes medical device programmer 24, implantable medical device (IMD) 324, lead extension 328, and leads 330A and 330B with respective sets of electrodes 332, 334. In the example shown in FIG. 1, electrodes 332, 334 of leads 330A, 330B are positioned to deliver electrical stimulation to a tissue site within brain 322, such as a deep brain site under the dura mater of brain 322 of patient 12A. In some examples, delivery of stimulation to one or more regions of brain 322, such as the subthalamic nucleus, globus pallidus or thalamus, may be an effective treatment to manage movement disorders, such as Parkinson's disease. Electrodes 332, 334 are also positioned to sense bioelectrical brain signals within brain 322 of patient 12A. In some examples, some of electrodes 332, 334 may be configured to sense bioelectrical brain signals and others of electrodes 332, 334 may be configured to deliver electrical stimulation to brain 322. In other examples, all of electrodes 332, 334 are configured to both sense bioelectrical brain signals and deliver electrical stimulation to brain 322.

IMD 324 includes a therapy module that includes a stimulation generator that generates and delivers electrical stimulation therapy to patient 12A via a subset of electrodes 332, 334 of leads 330A and 330B, respectively. The subset of electrodes 332, 334 that are used to deliver electrical stimulation to patient 12A, and, in some cases, the polarity of the subset of electrodes 332, 334, may be referred to as a stimulation electrode combination. In some examples, the stimulation electrode combination can be selected for a particular patient 12A and target tissue site (e.g., selected based on the patient condition), and/or based on one or more frequency domain characteristics of a bioelectrical brain signal sensed by one or more groups of electrodes 332, 334 that are associated with the stimulation electrode combination or another sensed patient parameter.

In some examples, bioelectrical signals sensed within brain 322 may reflect changes in electrical current produced by the sum of electrical potential differences across brain tissue. Examples of bioelectrical brain signals include, but are not limited to, electrical signals generated from local field potentials (LFP) sensed within one or more regions of brain 322, such as an electroencephalogram (EEG) signal, or an electrocorticogram (ECoG) signal. Local field potentials, however, may include a broader genus of electrical signals within brain 322 of patient 12A. Each of these signals may be correlated or calibrated with the identified patient behavior and used for feedback in controlling the delivery of therapy.

Electrical stimulation generated by IMD 324 may be configured to manage a variety of disorders and conditions. In some examples, the stimulation generator of IMD 324 is configured to generate and deliver electrical pulses to patient 12A via electrodes of a selected stimulation electrode combination. However, in other examples, the stimulation generator of IMD 324 may be configured to generate and deliver a continuous wave signal, e.g., a sine wave or triangle wave. In either case, a signal generator within IMD 324 may generate the electrical stimulation therapy for DBS according to a therapy program that is selected at that given time in therapy. In examples in which IMD 324 delivers electrical stimulation in the form of stimulation pulses, a therapy program may include a set of therapy parameter values, such as a stimulation electrode combination for delivering stimulation to patient 12A, pulse frequency, pulse width, and a current or voltage amplitude of the pulses. As previously indicated, the stimulation electrode combination may indicate the specific electrodes 332, 334 that are selected to deliver stimulation signals to tissue of patient 12A and the respective polarity of the selected electrodes.

IMD 324 may be implanted within a subcutaneous pocket above the clavicle, or, alternatively, the abdomen, back or buttocks of patient 12A, on or within cranium 14A or at any other suitable site within patient 12A. Generally, IMD 324 is constructed of a biocompatible material that resists corrosion and degradation from bodily fluids. IMD 324 may comprise a hermetic housing to substantially enclose components, such as a processor, therapy module, and memory.

As shown in FIG. 1, implanted lead extension 328 is coupled to IMD 324 via connector 3326 (also referred to as a connector block or a header of IMD 324). In the example of FIG. 1, lead extension 328 traverses from the implant site of IMD 324 and along the neck of patient 12A to cranium 14A of patient 12A to access brain 322. In the example shown in FIG. 1, leads 330A and 330B (collectively "leads 330") are implanted within the right and left hemispheres, respectively, of patient 12A in order deliver electrical stimulation to one or more regions of brain 322, which may be selected based on the patient condition or disorder controlled by therapy system 320. Other lead 330 and IMD 324 implant sites are contemplated. For example, IMD 324 may be implanted on or within cranium 14A, in some examples. In some examples, leads 330 may be implanted within the same hemisphere or IMD 324 may be coupled to a single lead.

Although leads 330 are shown in FIG. 1 as being coupled to a common lead extension 328, in other examples, leads 330 may be coupled to IMD 324 via separate lead extensions or directly to connector 326. Leads 330 may be positioned to deliver electrical stimulation to one or more target tissue sites within brain 322 to manage patient symptoms associated with a movement disorder of patient 12A. Leads 330 may be implanted to position electrodes 332, 334 at desired locations of brain 322 through respective holes in cranium 14A. Leads 330 may be placed at any location within brain 322 such that electrodes 332, 334 are capable of providing electrical stimulation to target tissue sites within brain 322 during treatment. For example, electrodes 332, 334 may be surgically implanted under the dura mater of brain 322 or within the cerebral cortex of brain 322 via a burr hole in cranium 14A of patient 12A, and electrically coupled to IMD 324 via one or more leads 330.

Example techniques for delivering therapy to manage a movement disorder are described in U.S. Pat. No. 8,121,694, to Molnar et al., entitled, "THERAPY CONTROL BASED ON A PATIENT MOVEMENT STATE," which was issued on Feb. 21, 2012, and which is incorporated herein by reference in its entirety. In some examples described by U.S. Pat. No. 8,121,694 to Molnar et al., a brain signal, such as an EEG or ECoG signal, may be used to determine whether a patient is in a movement state or a rest state. The movement state includes the state in which the patient is generating thoughts of movement (i.e., is intending to move), attempting to initiate movement or is actually undergoing movement. The movement state or rest state determination may then be used to control therapy delivery. For example, upon detecting a movement state of the patient, therapy delivery may be activated in order to help patient 12A initiate movement or maintain movement, and upon detecting a rest state of patient 12A, therapy delivery may be deactivated or otherwise modified.

In the example shown in FIG. 1, electrodes 332, 334 of leads 330 are shown as ring electrodes. Ring electrodes may be used in DBS applications because they are relatively simple to program and are capable of delivering an electrical field to any tissue adjacent to electrodes 332, 334. In other examples, electrodes 332, 334 may have different configurations. For example, in some examples, at least some of the electrodes 332, 334 of leads 330 may have a complex electrode array geometry that is capable of producing shaped electrical fields. The complex electrode array geometry may include multiple electrodes (e.g., partial ring or segmented electrodes) around the outer perimeter of each lead 330, rather than one ring electrode. In this manner, electrical stimulation may be directed in a specific direction from leads 330 to enhance therapy efficacy and reduce possible adverse side effects from stimulating a large volume of tissue. In some examples, a housing of IMD 324 may include one or more stimulation and/or sensing electrodes. In alternative examples, leads 330 may have shapes other than elongated cylinders as shown in FIG. 1. For example, leads 330 may be paddle leads, spherical leads, bendable leads, or any other type of shape effective in treating patient 12A and/or minimizing invasiveness of leads 330.

In some examples, IMD 324 includes a memory (shown in FIG. 3) to store a plurality of therapy programs that each define a set of therapy parameter values. In some examples, IMD 324 may select a therapy program from the memory based on various parameters, such as sensed patient parameters and the identified patient behaviors. IMD 324 may generate electrical stimulation based on the selected therapy program to manage the patient symptoms associated with a movement disorder.

External programmer 24 wirelessly communicates with IMD 324 as needed to provide or retrieve therapy information. Programmer 24 is an external computing device that the user, e.g., a clinician and/or patient 12A, may use to communicate with IMD 324. For example, programmer 24 may be a clinician programmer that the clinician uses to communicate with IMD 324 and program one or more therapy programs for IMD 324. Alternatively, programmer 24 may be a patient programmer that allows patient 12A to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 324.

When programmer 24 is configured for use by the clinician, programmer 24 may be used to transmit initial programming information to IMD 324. This initial information may include hardware information, such as the type of leads 330 and the electrode arrangement, the position of leads 330 within brain 322, the configuration of electrode array 332, 334, initial programs defining therapy parameter values, and any other information the clinician desires to program into IMD 324. Programmer 24 may also be capable of completing functional tests (e.g., measuring the impedance of electrodes 332, 334 of leads 330).

The clinician may also store therapy programs within IMD 324 with the aid of programmer 24. During a programming session, the clinician may determine one or more therapy programs that may provide efficacious therapy to patient 12A to address symptoms associated with the patient condition, and, in some cases, specific to one or more different patient states, such as a sleep state, movement state, or rest state. For example, the clinician may select one or more stimulation electrode combination with which stimulation is delivered to brain 322. During the programming session, patient 12A may provide feedback to the clinician as to the efficacy of the specific program being evaluated or the clinician may evaluate the efficacy based on one or more physiological parameters of patient 12A (e.g., muscle activity or muscle tone). Alternatively, the identified patient behavior from video information 50 may be used as feedback during the initial, and subsequent programming sessions. Programmer 24 may assist the clinician in the creation/identification of therapy programs by providing a methodical system for identifying potentially beneficial therapy parameter values.

Programmer 24 may also be configured for use by patient 12A. When configured as a patient programmer, programmer 24 may have limited functionality (compared to a clinician programmer) in order to prevent patient 12A from altering critical functions of IMD 324 or applications that may be detrimental to patient 12A. In this manner, programmer 24 may only allow patient 12A to adjust values for certain therapy parameters or set an available range of values for a particular therapy parameter.

Programmer 24 may also provide an indication to patient 12A when therapy is being delivered, when patient input has triggered a change in therapy or when the power source within programmer 24 or IMD 324 needs to be replaced or recharged. For example, programmer 24 may include an alert LED, may flash a message to patient 12A via a programmer display, generate an audible sound or somatosensory cue to confirm patient input was received, e.g., to indicate a patient state or to manually modify a therapy parameter.

Therapy system 320 may be implemented to provide chronic stimulation therapy to patient 12A over the course of several months or years. In other examples, however, system 320 may also be employed on a trial basis to evaluate therapy before committing to full implantation. If implemented temporarily, some components of system 320 may not be implanted within patient 12A. For example, patient 12A may be fitted with an external medical device, such as a trial stimulator, rather than IMD 324. The external medical device may be coupled to percutaneous leads or to implanted leads via a percutaneous extension. If the trial stimulator indicates DBS system 320 provides effective treatment to patient 12A, the clinician may implant a chronic stimulator within patient 12A for relatively long-term treatment.

IMD 324 may determine a therapy based on selection of one or more therapy parameter values (e.g., a set of therapy parameters or a therapy program) that at least partially define the therapy. In other examples, other computing devices may be configured to determine the therapy based on the identified patient behavior (e.g., movement disorder) or other sensed parameters of the patient. For example, a networked server, programmer 24, or any other computing device may determine the therapy. The therapy may include one or more of electrical stimulation therapy, drug delivery therapy (e.g., drug delivered from an implantable or external drug pump), or oral medication therapy.

Although IMD 324 is described as delivering electrical stimulation therapy to brain 322, IMD 324 may be configured to direct electrical stimulation to other anatomical regions of patient 12A. In other examples, system 320 may include an implantable drug pump in addition to, or in place of, electrical stimulator 324. Further, as described with respect to FIG. 2, an IMD may provide other electrical stimulation such as spinal cord stimulation to treat a movement disorder.

Figure 2:
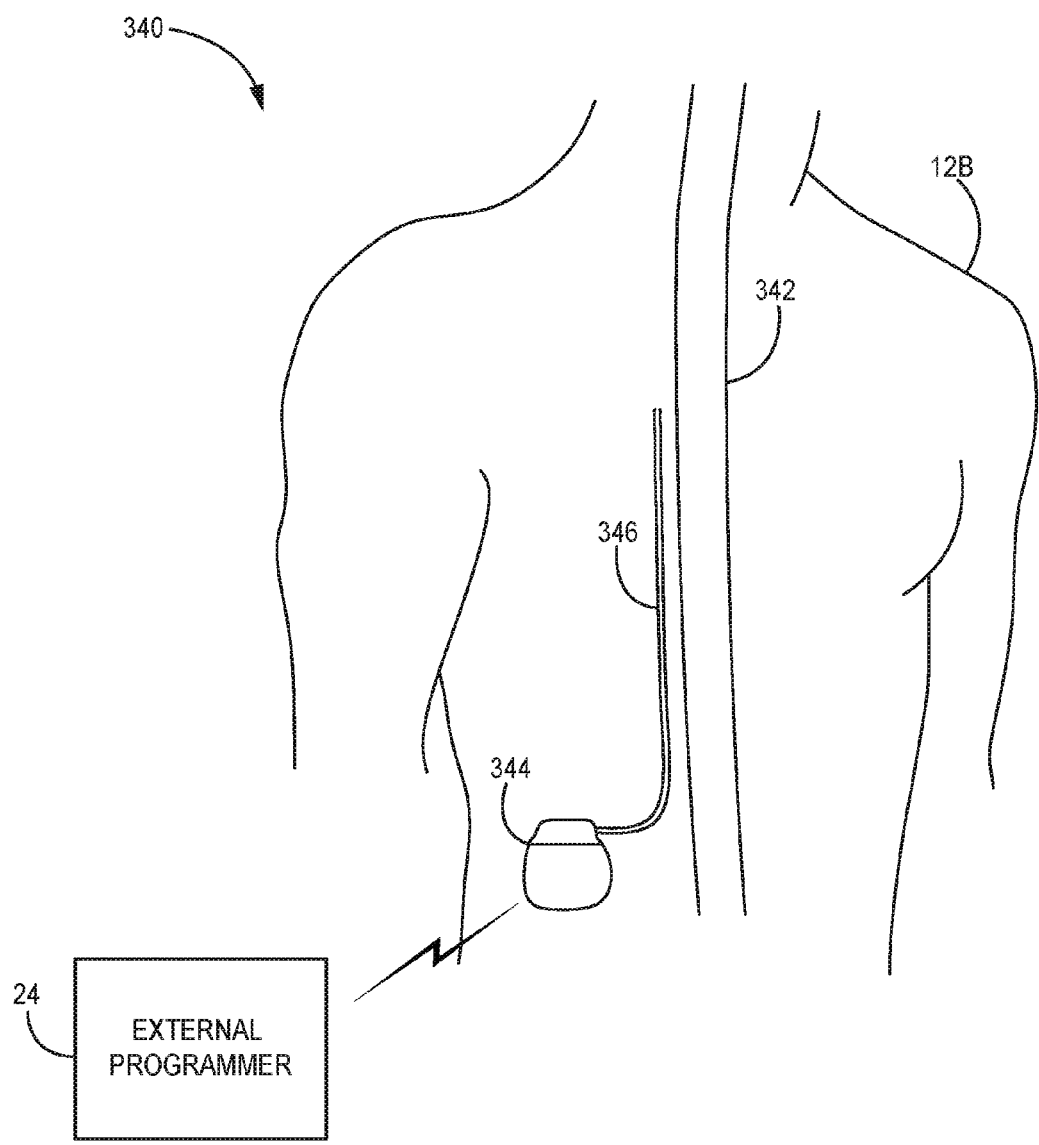
FIG. 2 is a conceptual diagram illustrating an example system that includes an IMD configured to deliver spinal cord stimulation (SCS) to a patient.

FIG. 2 is a conceptual diagram illustrating example system 340 that includes IMD 344 configured to deliver spinal cord stimulation (SCS) to a patient 12B. Although the particular example of FIG. 2 is described herein with respect to SCS, aspects of this disclosure may be applicable with respect to other types of electrical stimulation, such as pelvic floor stimulation, gastric stimulation, and various others. Patient 12B may be similar to patient 12A of FIG. 1.

As shown in FIG. 2, system 340 includes an IMD 344 and external programmer 24 shown in conjunction with a patient 12B, who is ordinarily a human patient. In the example of FIG. 2, IMD 344 is an implantable electrical stimulator that delivers neurostimulation therapy to patient 12B, e.g., for relief of chronic pain or other symptoms such as abnormal movements. Generally, IMD 344 may be a chronic electrical stimulator that remains implanted within patient 12B for weeks, months, or even years. IMD 344 may be similar to IMD 324 of FIG. 1. In the example of FIG. 2, IMD 344 and lead 346 may be configured for delivering SCS therapy. In other examples, IMD 344 may be a temporary, or trial, stimulator used to screen or evaluate the efficacy of electrical stimulation for chronic therapy. IMD 344 may be implanted in a subcutaneous tissue pocket, within one or more layers of muscle, or other internal location. IMD 344 may be coupled to one or more leads 346.

Electrical stimulation energy, which may be constant current or constant voltage based pulses, for example, is delivered from IMD 344 to one or more targeted locations within patient 12B via one or more electrodes (not shown) of lead 346. The parameters for a program that controls delivery of stimulation energy by IMD 344 may include information identifying which electrodes have been selected for delivery of stimulation according to a stimulation program, the combination of the selected electrodes, and the polarities of the selected electrodes, i.e., the electrode configuration for the program, and voltage or current amplitude, pulse frequency (or pulse rate), pulse shape, and pulse width of stimulation delivered by the electrodes. Electrical stimulation may be delivered in the form of stimulation pulses or continuous waveforms, for example.

In the example of FIG. 2, lead 346 is disposed within patient 12B, e.g., implanted within patient 12B. Lead 346 tunnels through tissue of patient 12B from along spinal cord 342 to a subcutaneous tissue pocket or other internal location where IMD 344 is disposed. Although lead 346 may be a single lead, lead 346 may include a lead extension or other segments that may aid in implantation or positioning of lead 346. In addition, a proximal end of lead 346 may include a connector (not shown) that electrically couples to a header of IMD 344. Although only one lead 346 is shown in FIG. 2, system 340 may include two or more leads, each coupled to IMD 344 and directed to similar or different target tissue sites. For example, multiple leads may be disposed along spinal cord 342 or leads may be directed to spinal cord 342 and/or other locations within patient 12B.

Lead 346 may carry one or more electrodes that are placed adjacent to the target tissue, e.g., spinal cord 342 for spinal cord stimulation (SCS) therapy. One or more electrodes may be disposed at or near a distal tip of lead 346 and/or at other positions at intermediate points along lead 346, for example. Electrodes of lead 346 transfer electrical stimulation generated by an electrical stimulation generator in IMD 344 to tissue of patient 12B. The electrodes may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), or any other type of electrodes capable of forming unipolar, bipolar or multipolar electrode combinations for therapy. In general, ring electrodes arranged at different axial positions at the distal ends of lead 346 will be described for purposes of illustration.

Similar to IMD 324 of FIG. 1, IMD 344 of FIG. 2 delivers electrical stimulation therapy to patient 12B via selected combinations of electrodes carried by lead 346. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 2, the target tissue for electrical stimulation delivered via lead 346 is tissue proximate spinal cord 342 (e.g., one or more target locations of the dorsal columns or one or more dorsal roots that branch from spinal cord 342). Lead 346 may be introduced into spinal cord 342 via any suitable region, such as the thoracic, cervical or lumbar regions. Stimulation of dorsal columns, dorsal roots, and/or peripheral nerves (e.g., afferent nerves) may, for example, prevent pain signals from traveling through spinal cord 342 and to the brain of the patient. Patient 12B may perceive the interruption of pain signals as a reduction in pain and, therefore, efficacious therapy results. For treatment of other disorders, lead 346 may be introduced at any exterior location of patient 12B.

Although lead 346 is described as generally delivering or transmitting electrical stimulation signals, lead 346 may additionally transmit electrical signals obtained via electrodes or various sensors carried by the lead from patient 12B to IMD 344 for monitoring. For example, IMD 344 may utilize detected nerve impulses or muscle impulses to diagnose the condition of patient 12B or adjust the delivered stimulation therapy. Lead 346 may thus transmit electrical signals to and from patient 12B.

A user, such as a clinician or patient 12B, may interact with a user interface of an external programmer 24 to program IMD 344. Programming of IMD 344 may refer generally to the generation and transfer of commands, programs, or other information to control the operation of IMD 344. In this manner, IMD 344 may receive the transferred commands and programs from programmer 24 to control stimulation therapy. For example, external programmer 24 may transmit programs, parameter adjustments, program selections, group selections, user input, or other information to control the operation of IMD 344, e.g., by wireless telemetry or wired connection.

Information may be transmitted between external programmer 24 and IMD 324 or 344. Therefore, IMD 324 or 344 and programmer 24 may communicate via wireless communication using any techniques known in the art. Examples of communication techniques may include, for example, radiofrequency (RF) telemetry and inductive coupling, but other techniques are also contemplated. In some examples, programmer 24 may include a communication head that may be placed proximate to the patient's body near the IMD 324 or 344 implant site in order to improve the quality or security of communication between IMD 324 or 344 and programmer 24. Communication between programmer 24 and IMD 324 or 344 may occur during power transmission or separate from power transmission.

Although IMD 324 and 344 are generally described as being implantable in FIGS. 1 and 2, techniques of this disclosure may also be applicable to external or partially external medical device in other examples. For example, IMD 324 or 344 may instead be configured as an external medical device coupled to one or more percutaneous medical leads. The external medical device may be a chronic, temporary, or trial electrical stimulator. In addition, an external electrical stimulator may be used in addition to one or more IMDs 340 or 344 to deliver electrical stimulation.

Figure 3:
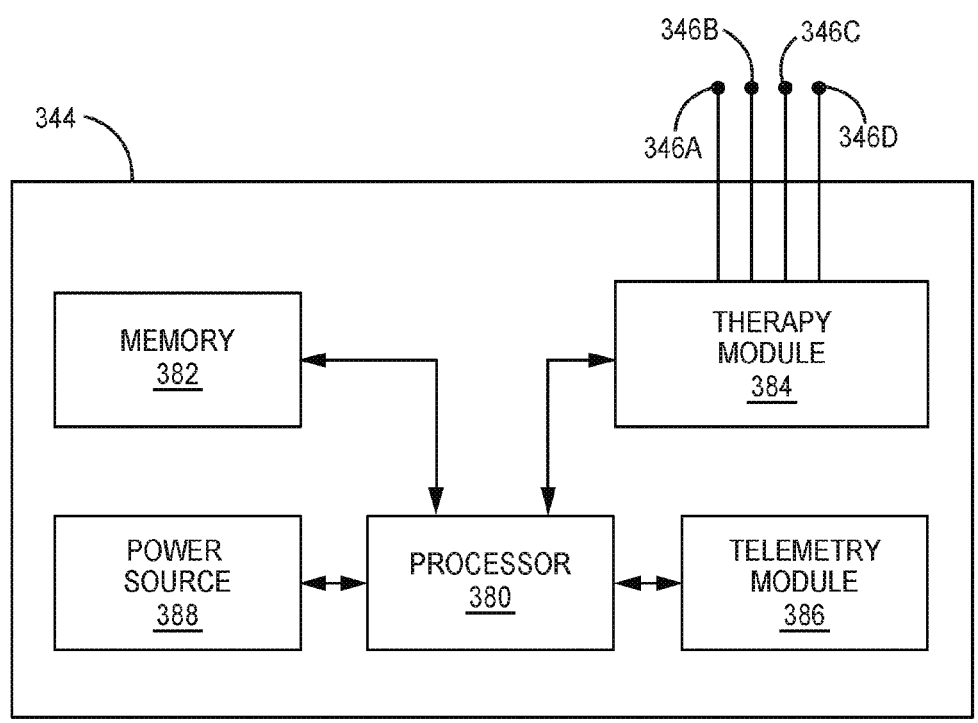
FIG. 3 is a block diagram of the example IMD of FIG. 2 for delivering spinal cord stimulation (SCS) therapy.

FIG. 3 is a block diagram illustrating example components of IMD 344 of FIG. 2 for delivering spinal cord stimulation (SCS) therapy. The same or similar components may be provided for IMD 324 for delivering deep brain stimulation therapy. As shown in the example of FIG. 3, IMD 344 includes processor 380, therapy module 384, power source 388, memory 382, and telemetry module 386. In other examples, IMD 344 may include a greater or fewer number of components. For example, IMD 344 may also include one or more sensors.

In general, IMD 344 may comprise any suitable arrangement of hardware, alone or in combination with software and/or firmware, to perform the various techniques described herein attributed to IMD 344 and processor 380. In various examples, IMD 344 may include one or more processors 30, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 344 also, in various examples, may include a memory 382, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although processor 380, therapy module 384, and telemetry module 386 are described as separate modules, in some examples, processor 380, therapy module 384, and telemetry module 386 may be functionally integrated. In some examples, processor 380, therapy module 384, and telemetry module 386 may correspond to individual hardware units, such as ASICs, DSPs, FPGAs, or other hardware units.

Memory 382 (e.g., a storage device) may store therapy programs or other instructions that specify therapy parameter values for the therapy provided by therapy module 384 and IMD 344. In some examples, memory 382 may also store instructions for communication between IMD 344 and programmer 24, or any other instructions required to perform tasks attributed to IMD 344. Memory 382 may also store feedback control instructions similar to feedback control 364 of IMD 324.

Generally, therapy module 384 may generate and deliver electrical stimulation under the control of processor 380. In some examples, processor 380 controls therapy module 384 by accessing memory 382 to selectively access and load at least one of the stimulation programs to therapy module 384. For example, in operation, processor 380 may access memory 382 to load one of the stimulation programs to therapy module 384. In such examples, relevant stimulation parameters may include a voltage amplitude, a current amplitude, a pulse frequency, a pulse width, a duty cycle, one or more spatial electrode movement patterns that define the combination of electrodes 346A, 346B, 346C, and 346D that therapy module 384 uses to deliver the electrical stimulation signal. Although therapy module 384 may be configured to generate and deliver electrical stimulation therapy via one or more of electrodes 346A, 346B, 346C, and 346D of lead 346, a different therapy module may be configured to provide different therapy to patient 12B, such as drug delivery therapy via a catheter. These and other therapies may be provided by IMD 344.

Therapy module 384, under the control of processor 380, generates stimulation signals for delivery to patient 12B via electrodes carried on one or more leads 346. An example range of electrical stimulation parameters that may be effective to provide therapy to a patient may include:

1. Frequency: between approximately 0.5 Hz and approximately 10000 Hz, more preferably between 5 Hz and 250 Hz, and more preferably between 30 Hz and 130 Hz.

2. Voltage Amplitude: between approximately 0.1 volts and approximately 50 volts, such as between approximately 0.5 volts and approximately 20 volts, or approximately 5 volts.

3. Current Amplitude: A current amplitude may be defined as the biological load in which the voltage is delivered. In a current-controlled system, the current amplitude, assuming a lower level impedance of approximately 500 ohms, may be between approximately 0.2 milliAmps to approximately 100 milliAmps, such as between approximately 1 milliAmps and approximately 40 milliAmps, or approximately 10 milliAmps. However, in some examples, the impedance may range between about 200 ohms and about 2 kiloohms.

4. Pulse Width: between approximately 10 microseconds and approximately 5000 microseconds, such as between approximately 100 microseconds and approximately 1000 microseconds, or between approximately 180 microseconds and approximately 450 microseconds.

IMD 344 also includes components to receive power from programmer 24 or a separate charging device to recharge a batter of power source 388. Power source 388 may include one or more capacitors, batteries, or other energy storage devices. IMD 344 may thus also include an inductive coil and a recharge module (both not shown) configured to manage the recharging session for power source 388. Although inductive coupling may be used to recharge power source 388, other wireless energy transfer techniques may alternatively be used. Alternatively, power source 388 may not be rechargeable.

Processor 380 may also control the exchange of information with programmer 24 using telemetry module 386. Telemetry module 386 may be configured for wireless communication using radio frequency protocols or inductive communication protocols. Telemetry module 386 may include one or more antennas configured to communicate with programmer 24, for example. Processor 380 may transmit operational information and receive therapy programs or therapy parameter adjustments via telemetry module 386. Also, in some examples, IMD 344 may communicate with other implanted devices, such as stimulators, control devices, or sensors, via telemetry module 386. For example, telemetry module 386 may receive user input, spatial electrode movement patterns, or other commands from programmer 24.

IMD 344 may include a sensing module (not shown) to sense one or more biological signals. Such signals may be used to control therapy in as described above. Sensing module may include various circuits for filtering and/or amplification of sensed biological signals such as electroencephalogram (EEG), electromyogram (EMG), electrocardiogram (ECG), local field potential (LFP), microelectrode recording (MER), electrocortiocographic (ECoG), evoked compound muscle action potential (ECMAP), and other types of signals. Additionally or alternatively, sensing module may include sensors to sense any other types of physiological signals, including accelerometers, glucose sensors, pH sensors and any other type of sensor suitable for sensing these or other such signals.

Figure 4:
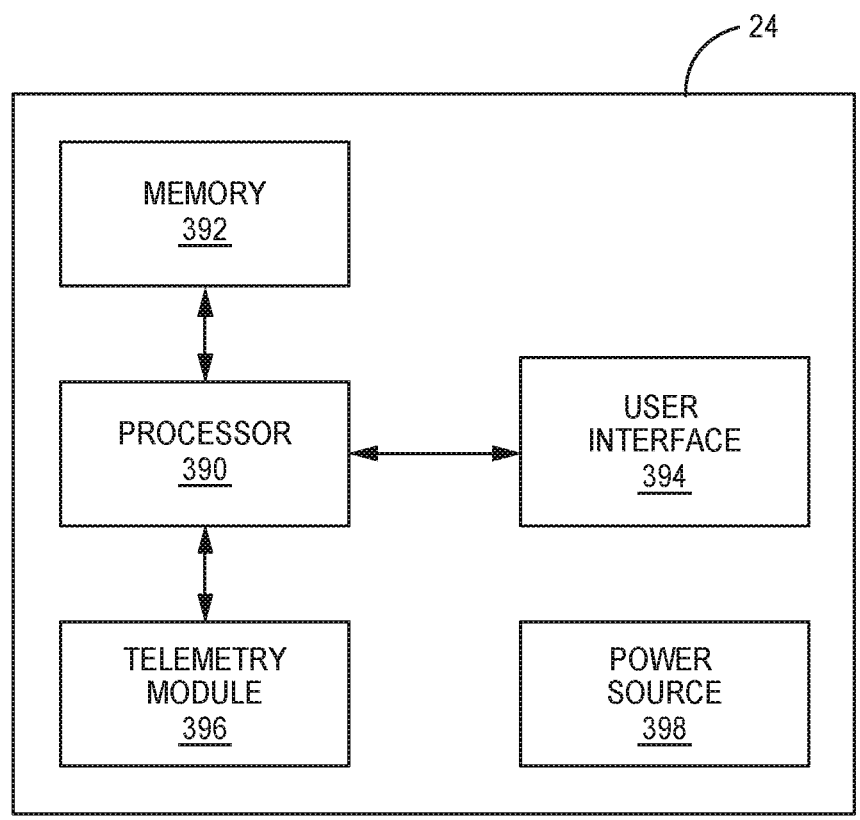
FIG. 4 is a block diagram of the external programmer of FIGS. 1 and 2.

FIG. 4 is a block diagram of external programmer 24 of FIGS. 1 and 2. Although programmer 24 may generally be described as a hand-held device, programmer 24 may be a larger portable device or a more stationary device. In addition, in other examples, programmer 24 may be included as part of an external charging device or include the functionality of an external charging device. As illustrated in FIG. 4, programmer 24 may include a processor 390, memory 392, user interface 394, telemetry module 396, and power source 398. Memory 392 may store instructions that, when executed by processor 390, cause processor 390 and external programmer 24 to provide the functionality ascribed to external programmer 24 throughout this disclosure.

In general, programmer 24 comprises any suitable arrangement of hardware, alone or in combination with software and/or firmware, to perform the techniques attributed to programmer 24, and processor 390, user interface 394, and telemetry module 396 of programmer 24. In various examples, programmer 24 may include one or more processors, such as one or more microprocessors, DSPs, ASICs, FPGAs, or any other equivalent integrated or discrete logic circuitry, as well as any combinations of such components. Programmer 24 also, in various examples, may include a memory 392, such as RAM, ROM, PROM, EPROM, EEPROM, flash memory, a hard disk, a CD-ROM, comprising executable instructions for causing the one or more processors to perform the actions attributed to them. Moreover, although processor 390 and telemetry module 396 are described as separate modules, in some examples, processor 390 and telemetry module 396 are functionally integrated. In some examples, processor 390 and telemetry module 396 correspond to individual hardware units, such as ASICs, DSPs, FPGAs, or other hardware units.

Memory 392 (e.g., a storage device) may store instructions that, when executed by processor 390, cause processor 390 and programmer 24 to provide the functionality ascribed to programmer 24 throughout this disclosure. For example, memory 392 may include instructions that cause processor 390 to obtain a parameter set from memory, select a spatial electrode movement pattern, or receive a user input and send a corresponding command to IMD 14, or instructions for any other functionality. In addition, memory 392 may include a plurality of programs, where each program includes a parameter set that defines stimulation therapy User interface 394 may include a button or keypad, lights, a speaker for voice commands or to detect other acoustic signatures, a display, such as a liquid crystal (LCD), light-emitting diode (LED), or organic light-emitting diode (OLED). User interface 394 may further include one or more accelerometers or other sensors to detect movement, positions, vibrations and the like, such as to detect a "tapping" on a case of programmer 24, shaking of the programmer, holding the programmer in a certain orientation such as up-side-down, moving the programmer in a particular direction, etc. User interface 394 may also include a camera interface to enable a user to capture an image that could be translated into input for use in programming the IMD. In some examples the display may be a touch screen. User interface 394 may be configured to display any information related to the delivery of stimulation therapy, identified patient behaviors, sensed patient parameter values, patient behavior criteria, or any other such information. User interface 394 may also receive user input via user interface 394. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, or the input may request some other change to the delivery of electrical stimulation, e.g., such as a change in current or voltage amplitude, a change in pulse rate, and/or a change in pulse width.

Telemetry module 396 may support wireless communication between IMD 14 and programmer 24 under the control of processor 390. Telemetry module 396 may also be configured to communicate with another computing device via wireless communication techniques, or direct communication through a wired connection. In some examples, telemetry module 396 may be substantially similar to telemetry module 358 of IMD 324 described herein, providing wireless communication via an RF or proximal inductive medium. In some examples, telemetry module 396 may include an antenna, which may take on a variety of forms, such as an internal or external antenna.

Examples of local wireless communication techniques that may be employed to facilitate communication between programmer 24 and IMD 324 include RF communication according to the 802.11 or Bluetooth specification sets or other standard or proprietary telemetry protocols. In this manner, other external devices may be capable of communicating with programmer 24 without needing to establish a secure wireless connection. As described herein, telemetry module 396 may be configured to transmit a spatial electrode movement pattern or other stimulation parameter values to IMD 324 for delivery of stimulation therapy.

In some examples, selection of therapy parameters or therapy programs may be transmitted to a medical device (e.g., IMD 324 or IMD 344) for delivery to patient 12. In other examples, the therapy may include medication, activities, or other instructions that patient 12 must perform themselves or a caregiver perform for patient 12. For example, in response to receiving an indication of an identified patient behavior or sensed patient parameter value, processor 390 may select a medication and/or dosage of the medication to treat the movement disorder. Processor 390 may control user interface 394 to display such information to the user. In some examples, programmer 24 may provide visual, audible, and/or tactile notifications that indicate there are new instructions. Programmer 24 may require receiving user input acknowledging that the instructions have been completed in some examples.

In other examples, programmer 24 may be configured to receive user input or indications of user input indicating the type of medication, dosage, and/or time the medication was taken by patient 12. Programmer 24 may create a log of the medications or other therapies manually taken by patient 12 in this manner. In some examples, programmer 24 may adjust electrical stimulation therapy and/or drug delivery therapy based on the medication that patient 12 has consumed. For example, programmer 24 may determine (e.g., adjust or maintain) one or more electrical stimulation therapy parameters based on the indication of the drug dosage taken by patient 12. This adjustment may be made due to physiological alterations of patient 12 by the medication.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to programmer 24, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between programmer 24 and a server. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

FIGS. 5A-5D are conceptual diagrams illustrating circular control elements 400A-400D respectively, which are examples of UI-based controls described herein. With reference to the example programmer 24 of FIG. 4, any of circular control elements 400A-400D may be displayed on a display of user interface 394. Circular control elements 400A-400D may display, and permit adjustment of, one or more parameter values for controlling therapy delivered by IMD 324 or 344. While described with respect to controlling therapy delivered by IMD 324 or 344 for purposes of example, it will be appreciated that in various examples, circular control elements 400A-400D may be used to control different types of parameters, via various types of medical devices, in accordance with aspects of this disclosure. As examples, circular control elements 400A-400D may be used to control parameters associated with external neurostimulators (ENSs), devices that adjust a patient's posture, drug delivery pumps, and various others.

For each of example circular control elements 400A-400D the present value of the parameter is indicated by portion of circular track 404 that is filled in. Other visual techniques to indicate the present value of the parameter are contemplated. Additionally, each of circular control elements 400A-400D displays a desired parameter value, as denoted by a knob 402, shown in FIGS. 5A-5D. More specifically, the clinician may set a desired value by dragging the knob around a circular track 404 to the desired value. Hence, the desired value may be a target value (e.g., target amplitude, target pulse rate, or target pulse width) that the user may wish the IMD to use for delivery of therapy. In turn, the current position of knob 402 along circular track 404 may represent the desired value.

Figure 5:
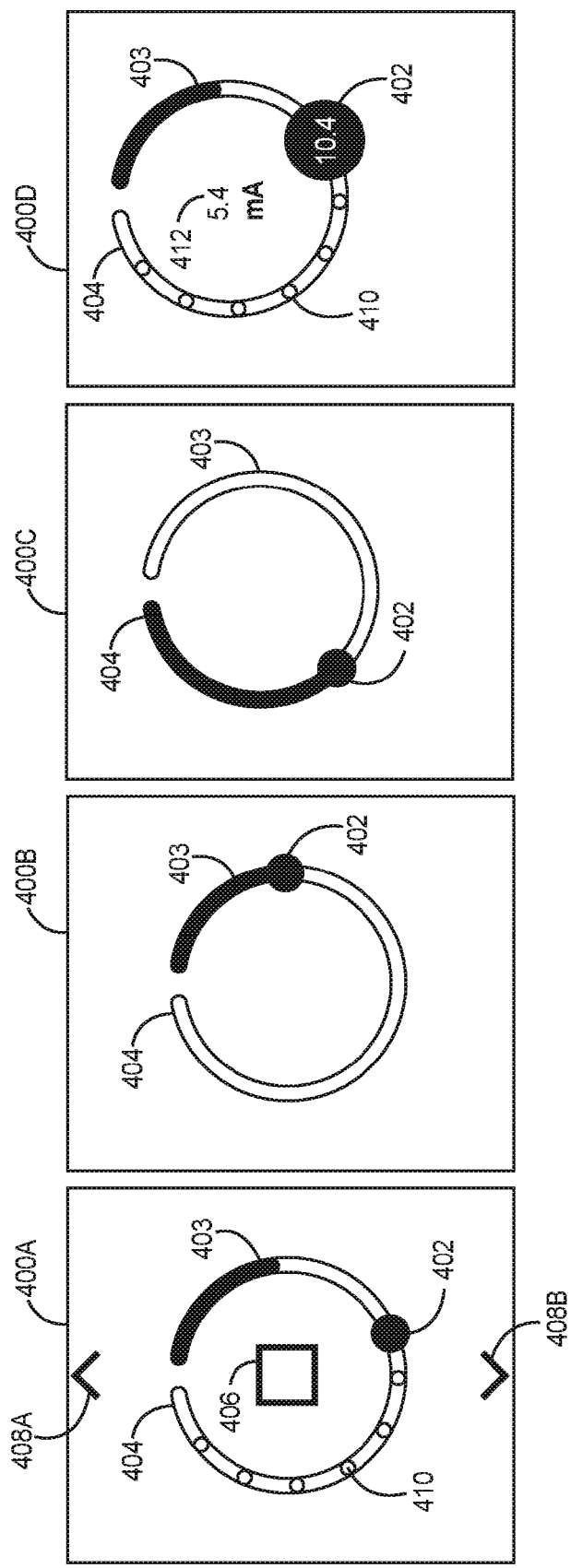
FIGS. 5A-5D are conceptual diagrams illustrating a circular control element, which are examples of UI-based controls described herein.

In the example of FIG. 5A, circular control element 400A also includes a stop button 406, which is an example of an on/off control. The user, e.g., a clinician, may activate therapy to ramp from the present value to the desired, i.e., target value, e.g., by clicking on a button (e.g., stop button 406) positioned at or near the center of circular control element 400A. The clinician may click on stop button 406 at the center of circular control element 400A to halt the change in the parameter value before the parameter value reaches the originally-set desired value, denoted by the position of knob 402. Programmer 24 may change the appearance of stop button 406 or may replace stop button 406 with a different UI element, depending on the mode.

For example, the button may appear as a play arrow before the pertinent parameter (e.g., amplitude, pulse rate, or pulse width) is ramped from the present value to the desired value is started, and then appear as a pause or stop button while the parameter ramps from the present value to the desired value. By halting the change in the parameter value, the clinician may leave the parameter value at the present value or at whatever intermediate value to which the parameter has been adjusted, i.e., an intermediate value between the present value and the desired value.

Additionally, circular control element 400A includes two "fine adjust" buttons 408A and 408B (alternatively, "fine adjust arrows"), as shown in FIG. 5A. The clinician may click each of the fine adjust buttons to change the parameter value incrementally. For example, the clinician may click upper fine adjust button 408A to increase the parameter value by a predetermined, discrete value. Conversely, the clinician may click lower fine adjust button 408B to decrease the parameter value by a discrete value. In various examples, both fine adjust buttons 408A and 408B may be associated with the same predetermined, discrete increment value, or with different discrete increment values, with respect to fine-tuning the desired parameter value. The discrete value may be fixed or adjusted by the user before fine-tuning is used. In some use cases, a clinician can set or adjust one or more of movement thresholds and/or brain activity hysteresis states.

FIG. 5A also includes progress track 403. Progress track 403 is displayed as a shaded portion of circular track 404. Progress track 403 may indicate the progress of the parameter ramping from a starting value up to the target value indicated by the current position of knob 402. For instance the end of progress track 403 (e.g., the extremity of progress track 403 when viewing progress track 403 in a clockwise direction) may represent the present parameter value, based on the calibration of circular 404. In the example of FIG. 5A, circular track 404 also includes individual calibration markers that represent discrete increments of parameter value increases from the desired value (represented by the position of knob 402), up to a maximum value (represented by the end of circular track 404, when traversing circular track 404 in a clockwise direction). Although circular control 400A includes several individual calibration markers, only a single instance (namely, calibration marker 410) is called out in FIG. 5A for ease of illustration purposes.

FIG. 5B represents an alternate design of the circular controls provided by aspects of this disclosure. FIG. 5B illustrates circular control 400B, with circular track 404, which includes knob 402 and progress track 403. FIG. 5C represents yet another alternate design, circular control 400C, in which the shading scheme of circular control 400B of FIG. 5B is reversed.

FIG. 5D illustrates still another alternate design of the circular controls of this disclosure, namely circular control 400D. Similar to circular control 400A of FIG. 5A, circular control 400D includes circular track 404 with knob 402, progress track 403, and calibration marker 410 (along with other individual calibration markers). However, in the example of circular control 400D, knob 402 includes a visual indication of the numeric value of the desired value set by the position of knob 402. In the specific example of FIG. 5A, the desired value represented by the position of knob 402, as reflected in the included visual indication, is 10.4 units (e.g., 10.4 mA). Circular control 400D of FIG. 5D also includes present value indicator 412. Present value indicator 412 includes a visual indication of the numeric value of the present value (that is, the value at this moment in time) of the pertinent parameter. For instance, the numeric value reflected by present value indicator 412 may correspond to the position of the end (traversing in clockwise direction) of progress track 403, based on the calibration scheme of circular track 404. In the specific example of FIG. 5A, the numeric value shown by present value indicator 412 is 5.4 mA, which may correspond to the current position of progress track 403 along circular track 404.

FIGS. 5A-5D illustrate example use cases in which a clinician uses circular control elements 400A-400D to increase a parameter value from a lower (e.g., present) value to a higher (e.g., desired) value. However, it will be appreciated that, in various use case scenarios, circular control elements 400A-400D may be used to decrease a parameter value from a higher (e.g., present) value to a lower (e.g., desired) value. For example, a clinician may drag knob 402 in opposite directions along circular track 404 of circular control elements 400A-400D to increase and decrease the parameter value to the desired value. According to the implementation illustrated in FIGS. 5A-5D, the clinician may drag knob 402 in a clockwise direction along circular track 404 to increase the present parameter value to a higher desired value. Conversely, according to the implementation illustrated in FIGS. 5A-5D, the clinician may drag knob 402 in a counter-clockwise direction along circular track 404 to decrease the present parameter value to a lower desired value. In this manner, aspects of this disclosure enable a clinician to use circular control elements 400A-400D to adjust therapy parameters in a variety of manners, thereby altering therapy to suit each individual patient.

Circular control elements 400A-400D may denote numeric values for a parameter value, including a minimum level and a maximum level for the parameter value. The minimum and maximum levels may be denoted, in relative terms, by a near-360-degree rotation along circular track 404 of circular control elements 400A-400D. In the examples of circular control elements 400A-400D, circular track 404 includes a separation between the starting point (which corresponds to a minimum parameter value), and the ending point (which corresponds to the maximum parameter value). In other implementations, a single point on circular track 404 of circular control element 400 may indicate both the minimum and maximum levels. In various use-case scenarios, the minimum and maximum levels for the parameter may be predetermined, or may be set in response to received user input(s).

In some implementations, a particular position on circular track 404 may also represent an "upper achievable limit," or a maximum value that may be set for the parameter using the circular control elements 400A-400D. In these implementations, the position on the circular track may function as a "stop," or a "lock," or a "governor" that may prevents the user from setting knob 402 to the maximum value represented by the ending point of circular track 404. Instead, the upper achievable limit position on circular track 404 may stop knob 402 at a particular value, overriding any attempts by the user to further increase the value of the parameter. The upper achievable value (which may also be referred to as a "maximum achievable value") may vary based on other parameters set with respect to the corresponding medical device.

Additionally, circular control elements 400A-400D may enable the clinician to set the desired parameter value (e.g., by placing or positioning knob 402 accordingly), and to change the parameter value toward the desired value in discrete steps. Circular control elements 400A and 400D illustrated in FIGS. 5A and 5D include individual calibration markers (such as calibration marker 410), that may function as discrete increments in which the clinician may increase/decrease the parameter value towards a desired value. The process of changing the parameter value toward the desired value in discrete steps is referred to herein as "ramping." For instance, ramping may refer to the process of incrementally increasing or decreasing the parameter value toward the desired value in discrete steps along circular track 404, such as in discrete increments indicated by individual calibration markers (e.g., calibration marker 410).

Although circular control elements 400A-400D are described herein with respect to modulating parameter values within a finite range, it will be appreciated that, in accordance with the techniques described herein, circular control elements 400A-400D may also be applied to entries in a list. For instance, circular control elements 400A-400D may be configured to enable the clinician to move knob 402 such that each incremental movement represents a selection of a particular option from a list of options. As one specific example, the list of options may include a total of eight options. In this example, each option may be positioned on the circumference of circular track 404 of circular control elements 400A-400D, at equal distances from one another, with each position being 45 degrees (as measured from the center of circular track 404) from each adjacent position. In such examples, circular control elements 400A-400D may enable the clinician to move knob 402 in discrete 45-degree increments, to select a particular option from the list.

Circular control elements 400A-400D may enable the clinician to adjust various types of parameters with respect to controlling operation of the corresponding medical device. In examples where circular control elements 400A-400D facilitate controlling operation of an IMD (e.g., IMDs 324 and/or 344 described above) that deliver electrical stimulation, circular control elements 400A-400D may be linked to various electrical waveform parameters. In various use-cases, the clinician may use circular control elements 400A-400D to adjust parameters such as voltage amplitude, current amplitude, frequency (e.g., as expressed by a sine wave), pulse rate (as expressed by a square wave), pulse width, and various others, with respect to electrical stimulation delivered by the associated IMD.

According to some examples, circular control elements 400A-400D may enable the clinician to select electrodes of the IMD, such as by moving knob 402 along the circumference of circular track 404. For instance, by moving knob 402 along the circumference of circular track 404, the clinician may change the anode/cathode combination through which electrical stimulation is currently delivered by the IMD.

In some examples, circular control elements 400A-400D may be configured to enable the clinician to adjust a number and/or spatial positions of a selected electrodes 332 and/or 334 along the respective leads 330 used for delivery of stimulation. According to some examples, the clinician may drag knob 402 along circular track 404 of any of circular control elements 400A-400D, to move one or more of a selected combination of electrodes 332, 334 axially along the respective leads 330. According to one example, the clinician may drag knob 402 in a clockwise direction along circular track 404 to move one or more of electrodes 332, 334 distally along the corresponding lead 330. According to this example, the clinician may drag knob 402 in a counterclockwise direction along circular track 404, to move one of electrodes 332, 334 proximally along the corresponding lead 330. In other words, according to this example implementation, the clinician may drag knob 402 along circular track 404 of circular control elements 400A-400D to activate the next electrode 332, 334 positioned on the respective lead 330 in either a distal or proximal direction, as the case may be. Additionally, in some examples where circular control elements 400A-400D are configured to control selection of electrodes 332, 334, circular control element 400 may include calibrated markers or other coincident indications along circular track 404 to map to the various electrodes 332, 334. For instance, the individual calibration markers that include calibration marker 410 in FIGS. 5A and 5D may correspond to individual electrodes in use cases in which circular controls 400A and/or 400D are configured to enable electrode selection and selection changes. Additionally, in some such examples, circular control elements 400A-400D may include graphic depictions to indicate which of electrodes 332, 334 is presently selected/activated, and to indicate which of electrodes 332, 334 is set as the desired electrode by the clinician. As one example, knob 402 of circular control elements 400A-400D may be positioned coincident with the desired electrode 332, 334.

While described above with respect to IMDs that deliver electrical stimulation (such as neurostimulation) to a patient, it will be appreciated that the techniques of this disclosure may be applied to different types of medical devices. As one example, circular control elements 400A-400D may control the operation of drug pumps. For instance, a clinician may adjust the position of knob 402 along the circumference of circular track 404 to ramp the dosage of medication delivered by an associated drug pump, or to ramp the time over which the medication is delivered by the drug pump. In other examples, circular control elements 400A-400D may enable a clinician to adjust the posture of a patient, by maneuvering a position of equipment, such as medical beds.

In various use-case scenarios, techniques of this disclosure may provide multiple controls, such as multiple instances of any one or more of circular control elements 400A-400D. In such implementations, each instance of the pertinent circular control element 400 may enable the clinician to adjust a different parameter associated with the medical device. Additionally, circular control elements 400A-400D may be calibrated differently in different use-cases, to accommodate varying clinician needs or patient needs. As one example, circular control elements 400A-400D may enable a greater number of (smaller) incremental movements, to support a more granular ramping of a parameter. Conversely, circular control elements 400A-400D may enable a lesser number of (larger) incremental movements, to support a coarse-grained ramping of the parameter. According to aspects of this disclosure, circular control elements 400A-400D may also be calibrated according to different units for the same measured quantity. As an example, if any of circular control elements 400A-400D is configured to control a parameter of time, then the pertinent circular control element 400 may be configured in any of hours, minutes, or seconds, to provide the clinician with varying levels of ramping granularity to choose from.

While the foregoing contemplates moving knob 402 along the circumference of circular track 404, using a dragging operation, other input mechanisms may be used to indicate the target position of knob 402 along circular track 404. For instance, user may be allowed to perform a "tapping" operation at a desired location on circular track 404 using a finger, a pointing device, or the like rather than utilize a dragging motion. In some cases, such "tapping" may only be allowed if programmer 24 is operating in a particular mode, such as a particular programming mode entered during a programming sequence or because of input designating the special mode.

Figure 10:
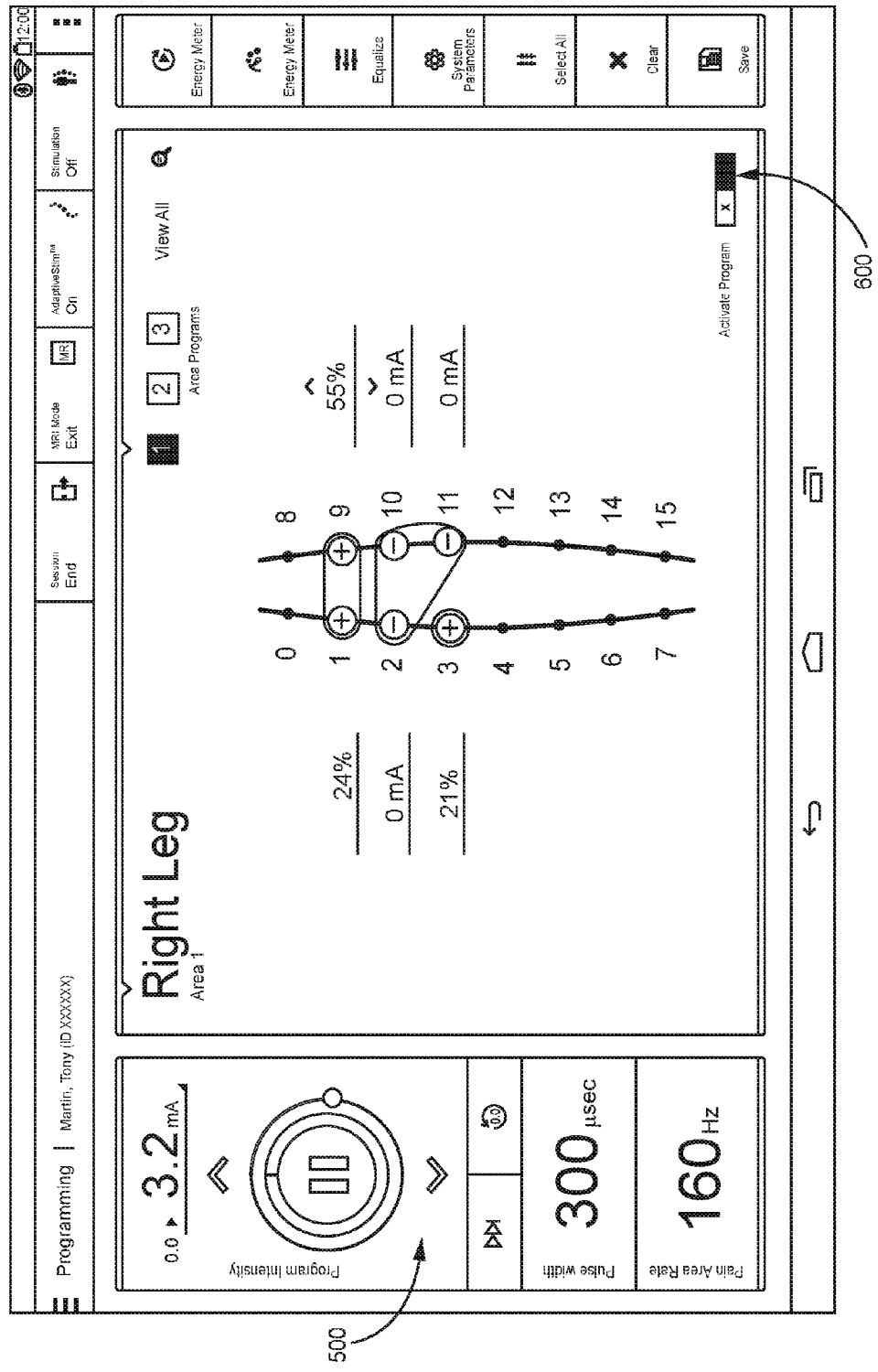

In other examples, a voice command may be used to move knob 402 to a desired position. The desired target position of knob 402 may be specified using an angular designation that provides an angle between either the starting or ending point of circular track, a designation associated with one of calibration markers 410, a percentage of distance from the beginning or the end of circular track 404, by indicating a particular value that corresponds to a location on circular track 404 (e.g., 3.2 mA as shown in FIG. 10 discussed below) or using any other command that will uniquely identify a location on the circular track. As in the example above, in some cases, such a voice command will only be allowed when the programmer is operating in a certain mode, such as a "hands-free" mode entered via some other type of user input. This type of "hands-free" control of programmer 24 may be desirable in a scenario wherein the clinician is operating in a sterile-field environment and programmer 24 is outside of the sterile field.

Figure 6:
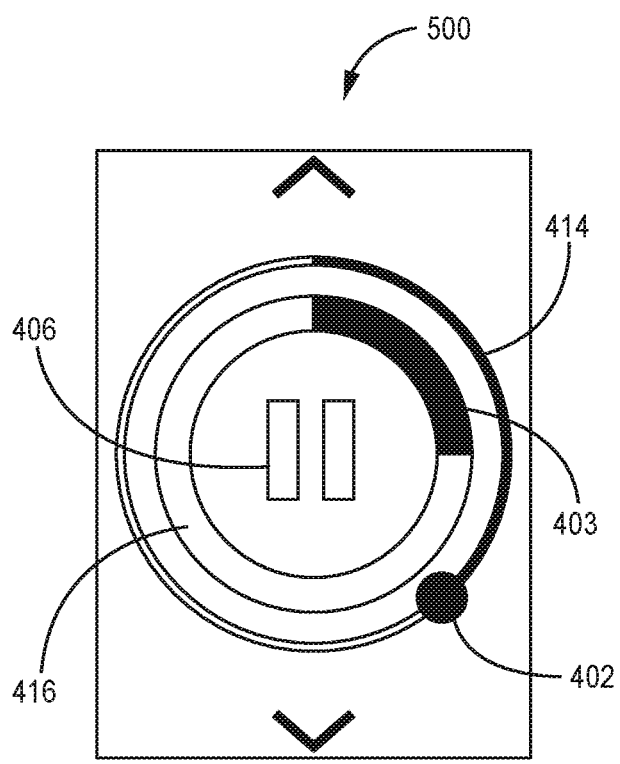
FIG. 6 is a conceptual diagram that illustrates another example circular control element, which is another example implementation of a UI-based control of this disclosure.

In yet other cases, a focused beam of light having a particular wavelength, as may be generated by a laser pointer, may be used to indicate the target position of knob 402. Such a light beam may be detected by a sensor of user interface 394. Any other type of user input may be provided instead of, or in addition to, dragging to specify the desired target position of knob 402 along the circumference of circular track. FIG. 6 is a conceptual diagram that illustrates circular control element 500, which is another example implementation of a UI-based control of this disclosure. Circular control element 500 may, in examples, be described as a modified version of circular control elements 400A-400D illustrated in FIGS. 5A-5D. In the example circular control element 500 illustrated in FIG. 6, visual treatment of circular control elements 400A-400D is modified to include two concentric rings. More specifically, circular control element 500 shows the desired parameter value indicated by the position of knob 402 along an outside (or "outer") ring 414, and shows the present parameter value using progress track 403 superimposed on an inside (or "inner") ring 416.

In the specific example of FIG. 6, the initial setting (or 'starting point') of knob 402 may be at a particular position on outer ring 414, denoting that the desired parameter value is currently set to the minimum level. The clinician may rotate, or otherwise drag knob 402, at various speeds, to various positions along outer ring 414, such as to the illustrated current position of knob 402. In various scenarios, the clinician may drag knob 402 at various speeds by a total 360 degrees around the circumference of outer ring 414, thus returning knob 402 to the starting point (e.g., at the topmost point of outer ring 414).

However, based on the 360-degree rotation, circular control element 500 may indicate that the desired parameter value is now set to the maximum level. For instance, progress bar 403 may cover the entire circumference of inner 416, upon the parameter value actually reaching the desired parameter value indicated by the position of knob 402. In other words, a 0-degree (zero-degree) angle or rotation of knob 402 along outer ring 414 corresponds to the "first item," namely, the minimum level on a "list" or "spectrum" of available parameter values. In this example, a 360-degree angle or rotation of knob 402 corresponds to the "last item," namely, the maximum level on the list or spectrum of parameter values. For values between the minimum and maximum values, techniques of this disclosure enable a linear interpolation to map the current angle of the position of knob 402 to corresponding values in the list, also referred to herein as the "controls value list." For instance, a 180-degree rotation of knob 402 along outer ring 414 may correspond to a parameter value that is at an average (e.g., median or mean) point or midpoint between the minimum and maximum values that are both represented by the 0-degree angled position of knob 402.

In accordance with aspects of this disclosure, a number of extensions are possible with respect to various base concepts described with respect to circular control elements 400A-

400D and 500 described above. For instance, the potential uses of circular control elements 400A-400D and 500 are not necessarily limited to numeric data and could also be used to select between images, names, dates, or other text options (e.g., from an option list, as described above). The concepts described above are also extendable beyond visual notifications of the state/parameter value to the clinician. On hardware (e.g., certain smartphones and tablet computers) that support vibration, haptic feedback can indicate to the clinician when the stop at 0 degrees and 360 degrees is reached (or "hit"), or when the desired value and the present value are equal.

According to various aspects of this disclosure, techniques used to calculate how the values are arrayed around the circular track 404 of circular control elements 400 or along outer and inner rings 414 and 416 of circular control element 500 may be adjusted as well. In other words, circular control elements 400 and 500 may be calibrated differently in different examples/implementations consistent with this disclosure. Other algorithms that could be used according to this disclosure (e.g., rather than linear interpolation) include an exponential function or a logarithmic function. Exponential and/or logarithmic functions may have the potential effect of positioning the values in a more concentrated fashion at either the lower (sharper) angles (e.g., 0-90 degrees) or the upper (greater or wider) angles (e.g., 270-360 degrees).

In some examples, one or more of circular control elements 400A-400D and 500 are referred to herein as widgets or, more specifically, as "parameter entry widgets." The parameter entry widget of this disclosure allows for moving quickly through a range of values. For example, a clinician may move quickly through a range of parameter values with respect to controlling a medical device. The parameter entry widget may capture a desired value that can be set (or is "settable") through a slider of the widget, and may display the present value of the parameter by filling in the area (e.g., the portion of the circular track's circumference) behind the knob. More specifically, the portion of circular track 404 or outer ring 414 that is "behind" knob 402 may refer to a portion of the circumference of the respective track/ring beginning at the position of knob 402, traversing the track/ring in counterclockwise fashion, up to the starting point of the track/ring. As described above, the starting point of the track/ring may coincide with the minimum and maximum parameter values that can be applied using the parameter entry widget. The buttons on top and bottom (e.g., fine adjustment buttons 408A and 408B of FIG. 5A) allow for fine adjustment of the desired value. In some implementations, one or more of circular control elements 400A-400D and 500 support an array of values, and may select the desired value by determining which value is closest to slider value set by the clinician (e.g., by placement of knob 402). According to these examples, the slider (e.g., knob 402) may then "snap" to the appropriate location representing the nearest value to the position at which the clinician placed knob 402.

An example documentation (e.g., in the format of software documentation) of the parameter entry widget is described in this paragraph and the included bullet points. The parameter entry widget implements the functionality to perform one or more selections between the values in an array, by moving a circular slider. The parameter entry widget keeps track of two values, namely, the current and desired values (e.g., as indicated by the ending point of progress track 403 and the position of knob 402, respectively). To use the widget, a clinician may instantiate (e.g. create an instance of) the widget, or get the instance of the widget from a predefined XML, layout. Then, the clinician may use the setValidValues to set the array of values to use in accordance with the widget. To register any changes to the widget, the clinician may pass an instance of IParameterAdjusted into the setParameterAdjusted method/function/subroutine. The widget provides callbacks for the following:

Parameter value changed—Called every time the slider moves

Parameter value set—Called when the slider is released and is set to a desired value or when the fine adjust buttons are pressed.

Stop requested—Called when the user presses the stop button

The stop button (e.g., stop button 406) can be shown or hidden by calling the setShowStop method. The widget will automatically set the color of the interior progress ring whenever the present value (or value at the current instant of time) does not match the desired value. The widget also supports showing a stop button in the middle which allows the user to stop any ramping that is in progress. The application controls when the button is displayed and what happens when it is clicked. The desired value is shown graphically on the outer ring 414, spanning a portion of the outer ring from the initial position of the outer ring 414, and traversing a clockwise route to the position of the knob 402. In some example implementations, the "desired value" portion of the outer ring circumference may be visually demarcated, such as by color-coding (e.g., by displaying the "desired value" portion of the outer ring circumference in blue, and displaying the remaining portion of the outer ring circumference in a different color or shade). Similarly, the present value is shown on the inner ring 416, as spanning the circumference of the inner ring 416, beginning at the initial position of the inner ring 416, and traversing a clockwise route to the calibration corresponding to the present value. In some implementations, the "current value" portion of the circumference of inner ring 416 may be visually demarcated, such as by color-coding (e.g., by displaying the "present value" portion of the inner ring circumference in white, and displaying the remainder of inner ring circumference in a different shade or color).

Colors and widths of the various circles can be modified by the application through the application of a different style. In some examples, the outer ring may be designated to represent the present value and the inner right may correspond with the "desired value".

FIGS. 7-11 are screenshots of example UIs illustrating use of a circular control element of this disclosure to operate an electrical stimulator. Taken in sequence, the UIs of FIGS. 7-11 illustrate an example of chronological operation of a circular control element to activate a stimulator and ramp up the amount of current passed through selected electrodes of the stimulator. The circular control elements illustrated in FIGS. 7-11 are, in various instances, example implementations of circular control element 500 described above with respect to FIG. 6. The UIs of FIGS. 7-11 may be displayed and operated via a number of computing devices, including tablet computers, personal digital assistants (PDAs), phones (including so-called "smartphones"), laptop computers (including so-called "netbooks" and "ultrabooks"), desktop computers, customized communication devices, and so on. Additionally, the computing device implementing the UIs of FIGS. 7-11 may be configured to communicate with the stimulator through various communication channels, including various wired and/or wireless links that enable the transmission and/or receipt of data. Such wired and/or wireless links may include one or both of physical or logical links.

Figure 7:
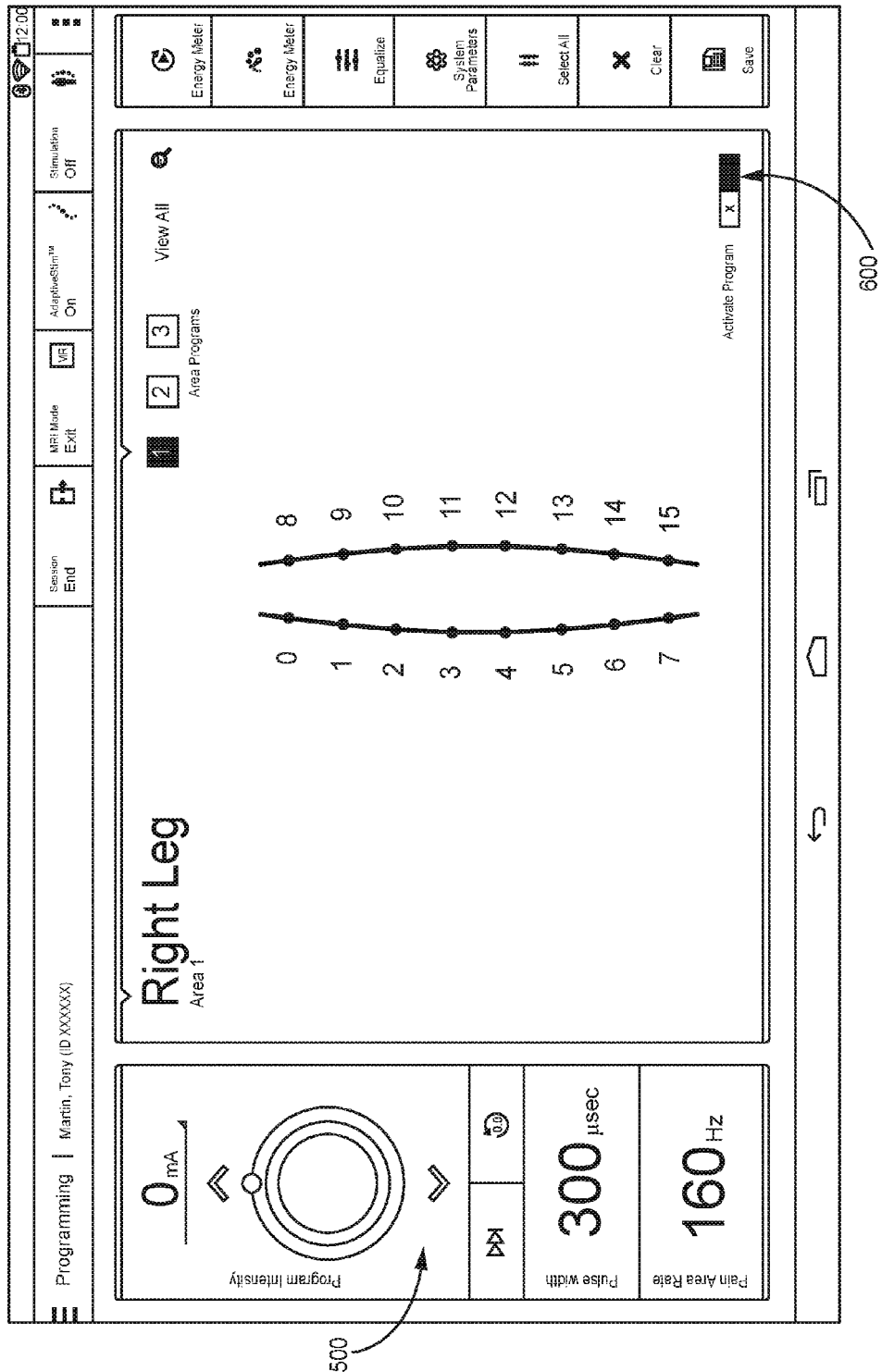
FIGS. 7-11 are screenshots of example UIs illustrating use of a circular control element of this disclosure to program an electrical stimulator.

Additionally, according to FIGS. 7-11, a clinician may use circular control element 500 to operate a two-lead stimulator, such as a stimulator that includes leads 330A and 330B which, in turn, include electrodes 332 and 334. In the specific example of FIG. 7, leads 330 include a total of 16 electrodes, identified by index values 0-15. As shown in FIG. 7, the two-lead stimulator may begin in an inactive activated state (either by default, or via deactivation input), with none of electrodes 332 and 334 selected for operation. In the example of FIG. 7, circular control element 500 is set to implement a default value of zero milliamps (0 mA) of current via electrodes 332 and 334. As shown in FIG. 7, the stimulator is configured to deliver stimulation for the right leg of a patient, and the pulse width and pain area rate are set to 300 microseconds (μsec) and 160 hertz (Hz), respectively, with respect to operation of the stimulator. Activation button 600 displays an inactive state, which may be toggled between active and inactive, to activate and deactivate, respectively, the currently viewed parameters for stimulator operation.

Figure 8:
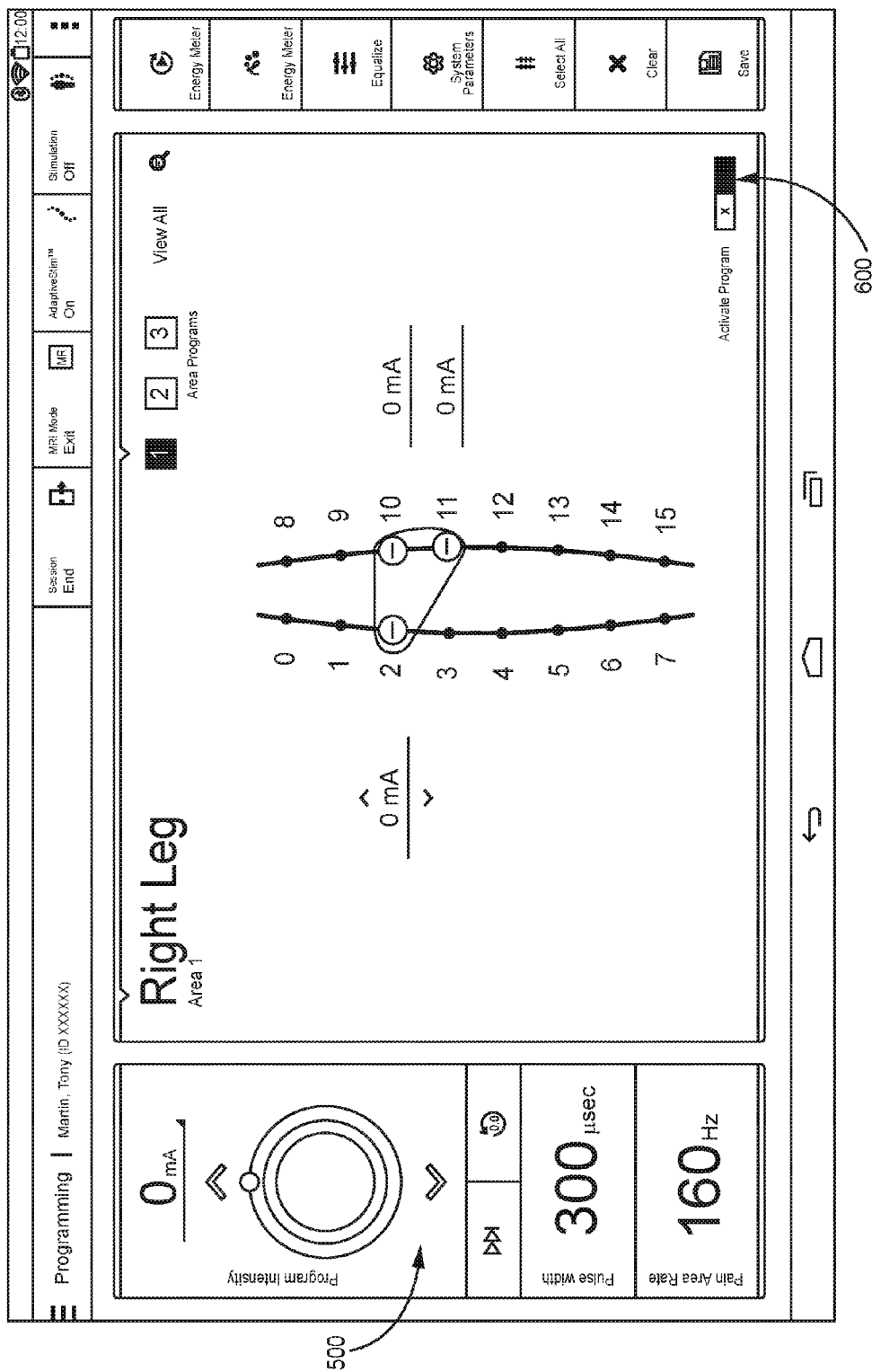

In the example of FIG. 8, the stimulator is activated, such as in response to user input received at activation button 600. In other examples, some other type of input may be used to initiate activation, such as a voice command, a laser prompt, input detected by a motion or position sensor, or any other type of input that may be sensed by user interface 394 that identifies the activation function. In some cases, programmer 24 may be conditioned to interpret the activation input based on prior mode information provided to designate entry into a specific programming mode. Additionally, three of electrodes 332 and 334 are selected in the example of FIG. 8. More specifically, three of electrodes 332 and 334 are selected to have a negative polarity, e.g., to function as cathodes. The selected electrodes 332 and 334 are identified by index values of 2, 10, and 11. As shown, in the example of FIG. 8, circular control 500 reflects a present value of 0 mA, as well as a desired value of 0 mA with respect to the current passed through electrodes 332 and 334.

Figure 9:
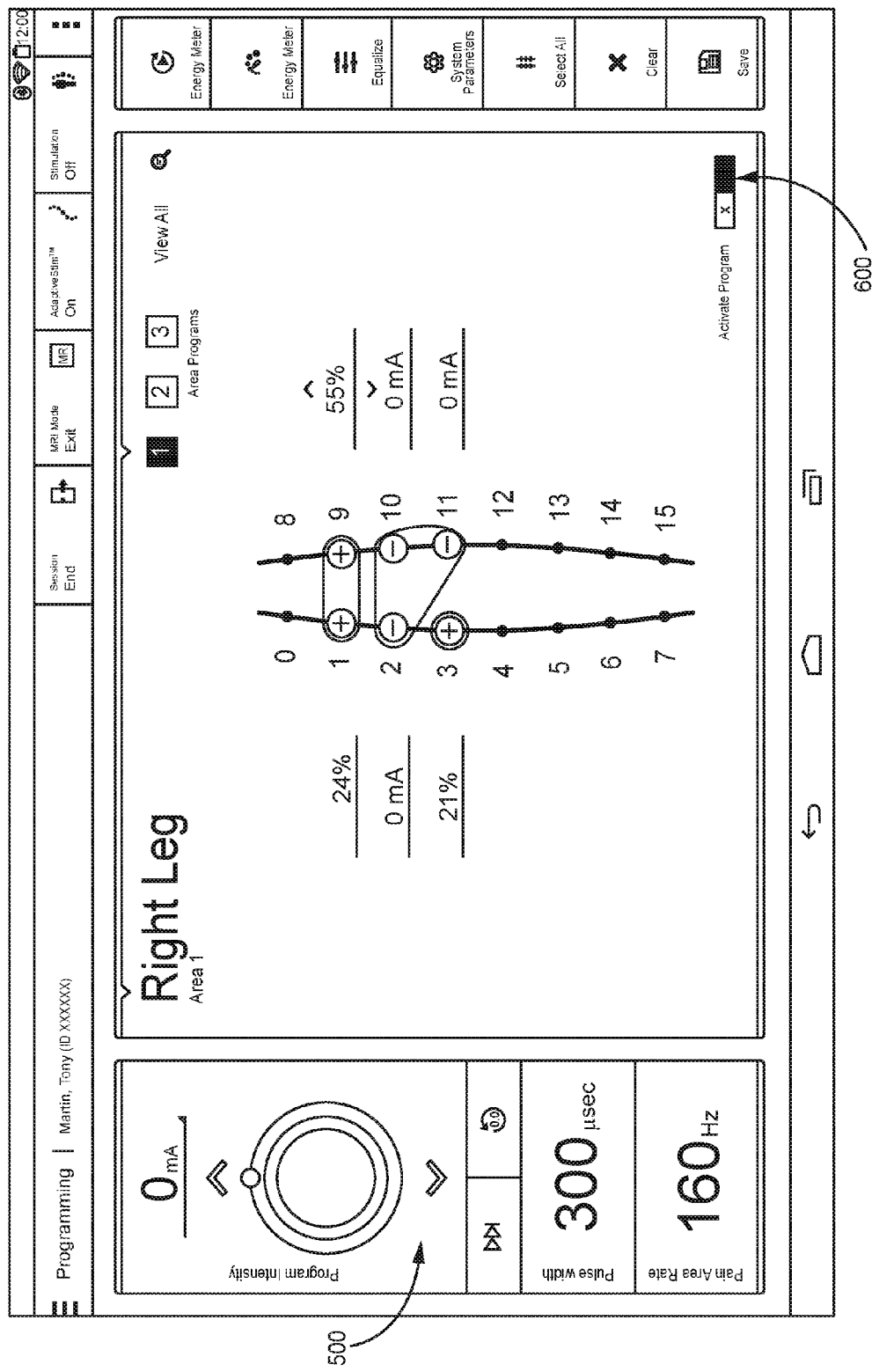

FIG. 9 illustrates an example UI in which a total of six of electrodes 332 and 334 are selected. More specifically, in the example of FIG. 9, the three negative-polarity electrodes 332, 334 selected in FIG. 8 remain selected. In addition, three more of electrodes 332 and 334 are selected in FIG. 9 as having a positive polarity (e.g., anodes). The three electrodes selected to have the positive polarity are identified by index values of 1, 3, and 9. As shown, the present and desired current values remain at 0 mA in the example of FIG. 9.

FIG. 10 illustrates an example UI in which the clinician uses circular control 500 to set the desired current level to a value of 3.2 mA. In the example of FIG. 10, the present current level implemented via electrodes 332 and 334 remains at 0 mA. As shown in FIG. 10, the present and desired current levels are illustrated in relative terms, using a graphical marker on the inner ring of circular control 500 to denote the present value (e.g., progress track 403), and using the position of knob 402 (e.g., as placed by the operating clinician) on the outer ring of circular control element 500. Additionally, circular control element 500 displays numerical values for each of the present and desired values, as well. In the example of FIG. 10, circular control element 500 also includes a "pause" button (shown in the center of circular control element 500 in this example), to enable the clinician to halt ramping of the implemented current while the current value gradually increases from 0 mA to 3.2 mA.

Figure 11:
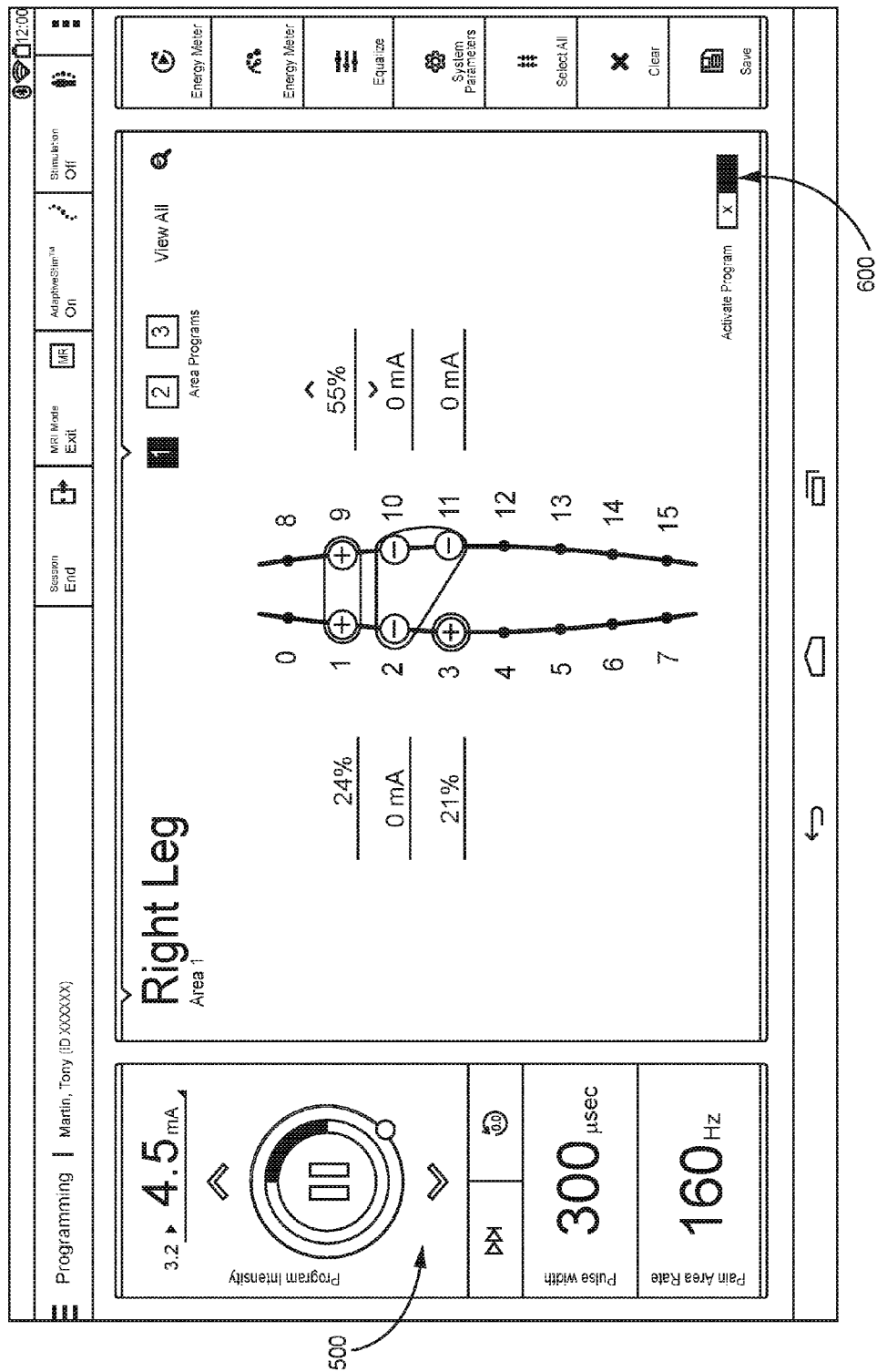

FIG. 11 illustrates an example UI in which the present value of the current applied through the stimulator has reached 3.2 mA, which was the desired current level set by a clinician in the example of FIG. 10. Additionally, in the example of FIG. 11, a clinician has set the desired current level to a new value of 4.5 mA.

Figure 12:
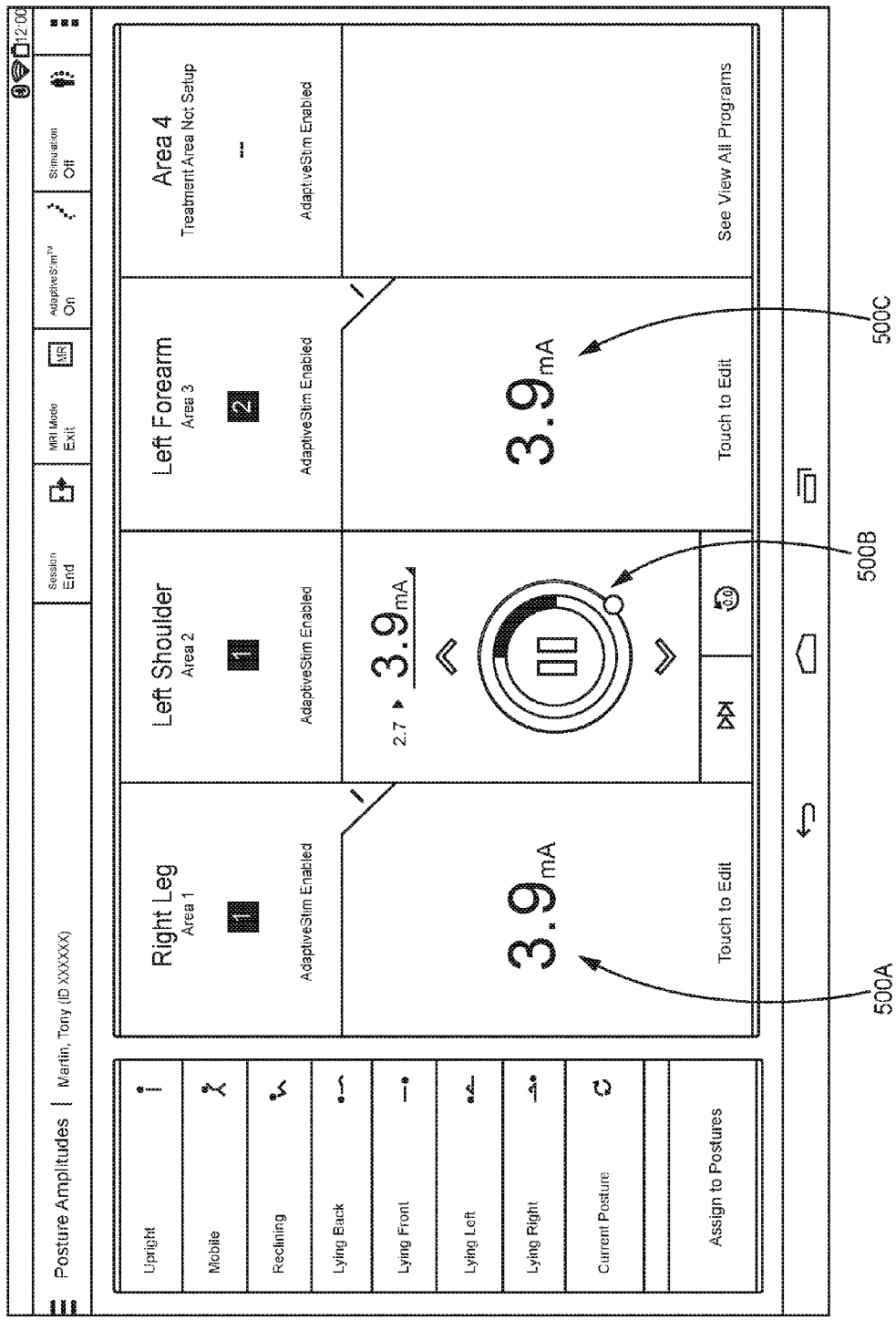
FIG. 12 is a screenshot of an example UI illustrating use of multiple instances of a circular control element of this disclosure to program a plurality of electrical stimulation programs for delivery by one or more electrical stimulators.

FIG. 12 is a screenshot of an example UI illustrating use of multiple instances of a circular control element of this disclosure to program a plurality of electrical stimulation programs (e.g., "Right Leg," "Left Shoulder," or "Left Forearm") for delivery by an IMD. In the example of FIG. 12, the UI includes three instances of circular control element 500, labeled as circular control elements 500A-500C. In the example of FIG. 12, circular control elements 500A and 500C display the desired current values set by a clinician (namely, 3.9 mA in each case). Circular control element 500B is either currently selected for parameter adjustment, or was the last selected one of circular control elements 500A-500C that was selected for parameter adjustment. Thus, the UI of FIG. 12 includes a display of the circular tracks of circular control element 500B, as well as numerical displays of the present and desired current values to be applied through the corresponding stimulator.

Figure 13:
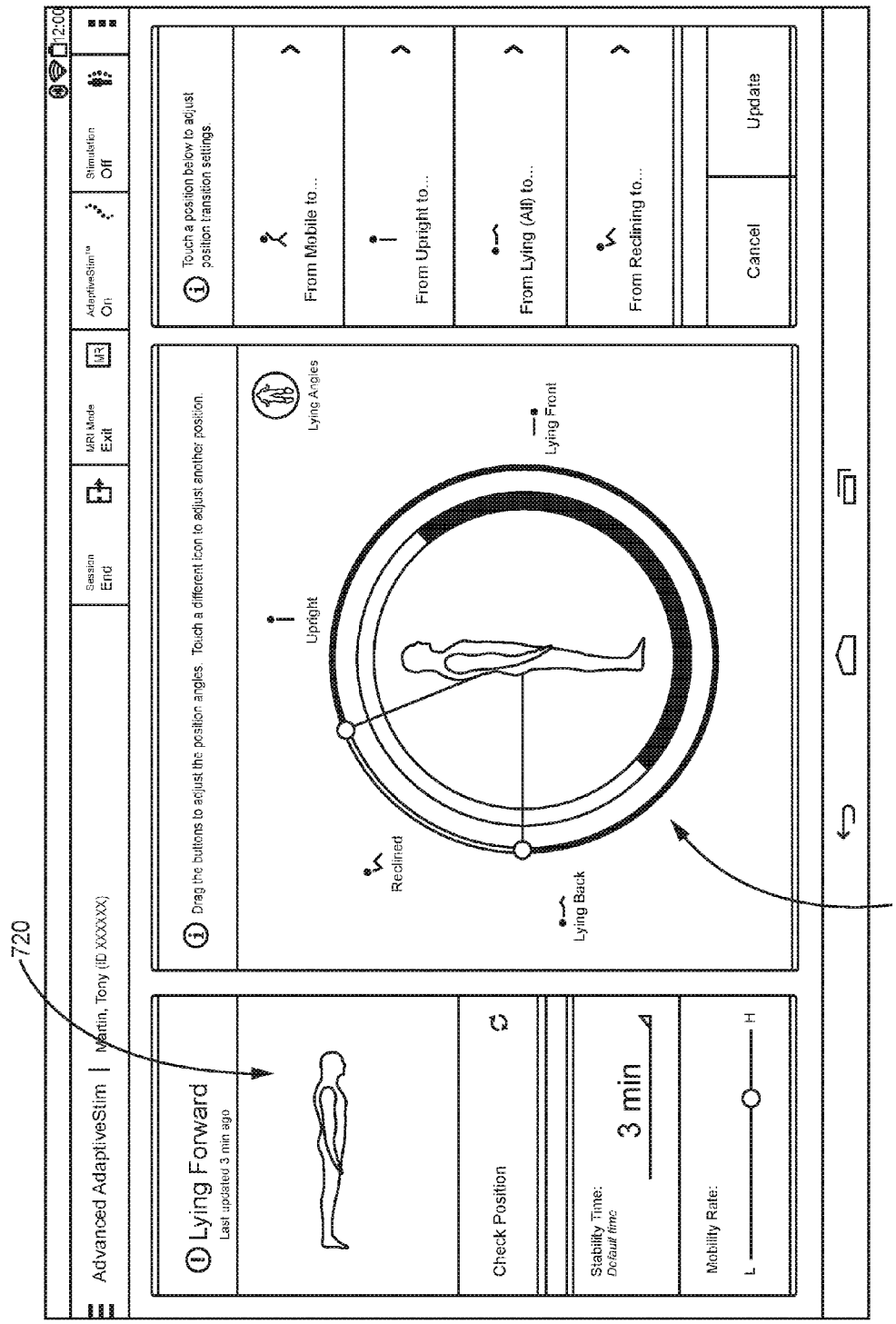
FIGS. 13 and 14 are screenshots of example UIs illustrating use of a circular control element of this disclosure to adjust postural parameters for operation of a medical device.
Figure 14:
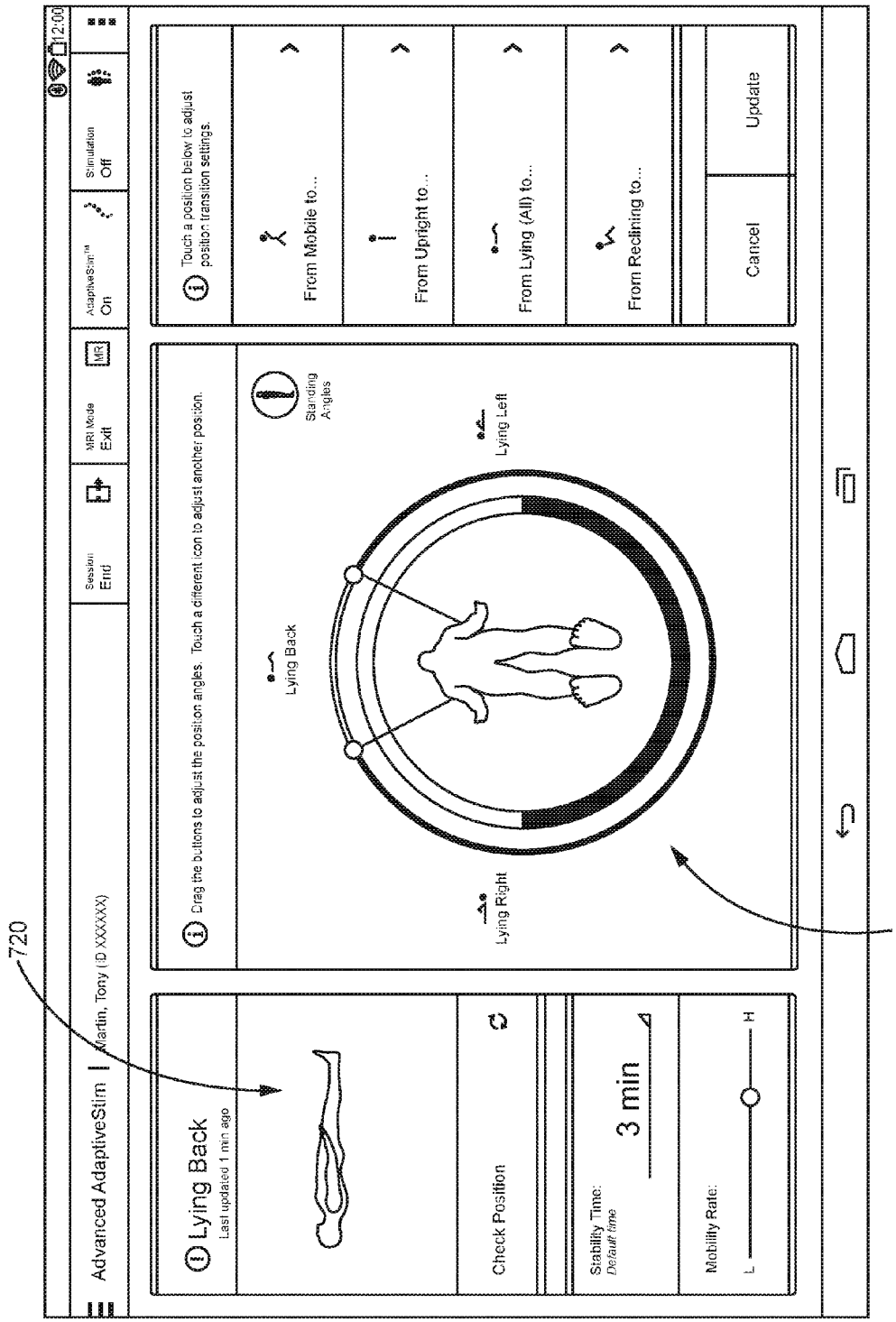

FIGS. 13 and 14 are screenshots of example UIs illustrating use of circular control elements 700A and 700B to adjust postural parameters, e.g., for operation of a posture-responsive medical device. For example, parameters for electrical stimulation or other therapies may be adjusted based on a sensed posture of the patient. Based on signals sensed by one or more posture sensors, e.g., accelerometers, an IMD may determine in which of a plurality of predefined posture states a patient currently is, and adjust the stimulation accordingly.

In the example of FIG. 13, the clinician may use circular control element 700A to change the angles or other parameters that define or demarcate different posture states or positions of the patient. In the illustrated example, circular control element 700A is used to change the angles that define the "lying forward" or "lying front" posture state of a patient, as shown by the graphical representation of a patient at current position 720. As shown in FIG. 13, the clinician may adjust the postural parameter for a variety of posture states, such as an "upright" position, a "lying back" position, and a "reclined" position. For example, the "lying forward" and "lying back" positions may be at a 180-degree angle from one another, while the "upright" position may be at 90-degrees from each of the "lying forward" and "lying back" positions. More specifically, the "upright" position may be an intermediate position between the "lying front" and "lying back" positions. Similarly, the "reclined" position may be an intermediate position between the "upright" and "lying back" positions. In one example, the "reclined" position may be at 45 degrees from each of the "upright" and the "lying back" positions.

The clinician may adjust the posture parameters coincident to represent posture zones for postures occupied by the patient. In this manner, a clinician may calibrate the posture parameter values to correspond to particular postures occupied by the patient, e.g., to calibrate the posture response of the therapy device. Posture-responsive therapy devices are described, for example, in U.S. Pat. No. 8,588,929, issued Nov. 19, 2013, U.S. Pat. No. 8,886,302, issued Nov. 11, 2014, and U.S. Pat. No. 8,175,720, issued May 8, 2012, to Skelton et al., the entire content of each of which is incorporated herein by reference.

FIG. 14 illustrates an example in which the clinician may adjust postural parameters between different "lying" positions of a patient using circular control element 700B. More specifically, the clinician may adjust the postural parameter between the options of a "lying back" position, a "lying right" position, and a "lying left" position. The "lying back" position may correspond to a patient lying on his/her back, while the "lying right" position may correspond to a patient lying on his/her right side (e.g., right shoulder and hip), and the "lying left" position may correspond to a patient lying on his/her left side (e.g. left shoulder and hip). Using a circular UI element, as illustrated in FIGS. 13 and 14, a clinician may adjust posture parameters to correspond to particular postures. In this manner, the clinician may adjust the response of a device, in determining postures, to sensed postures.

Figure 15:
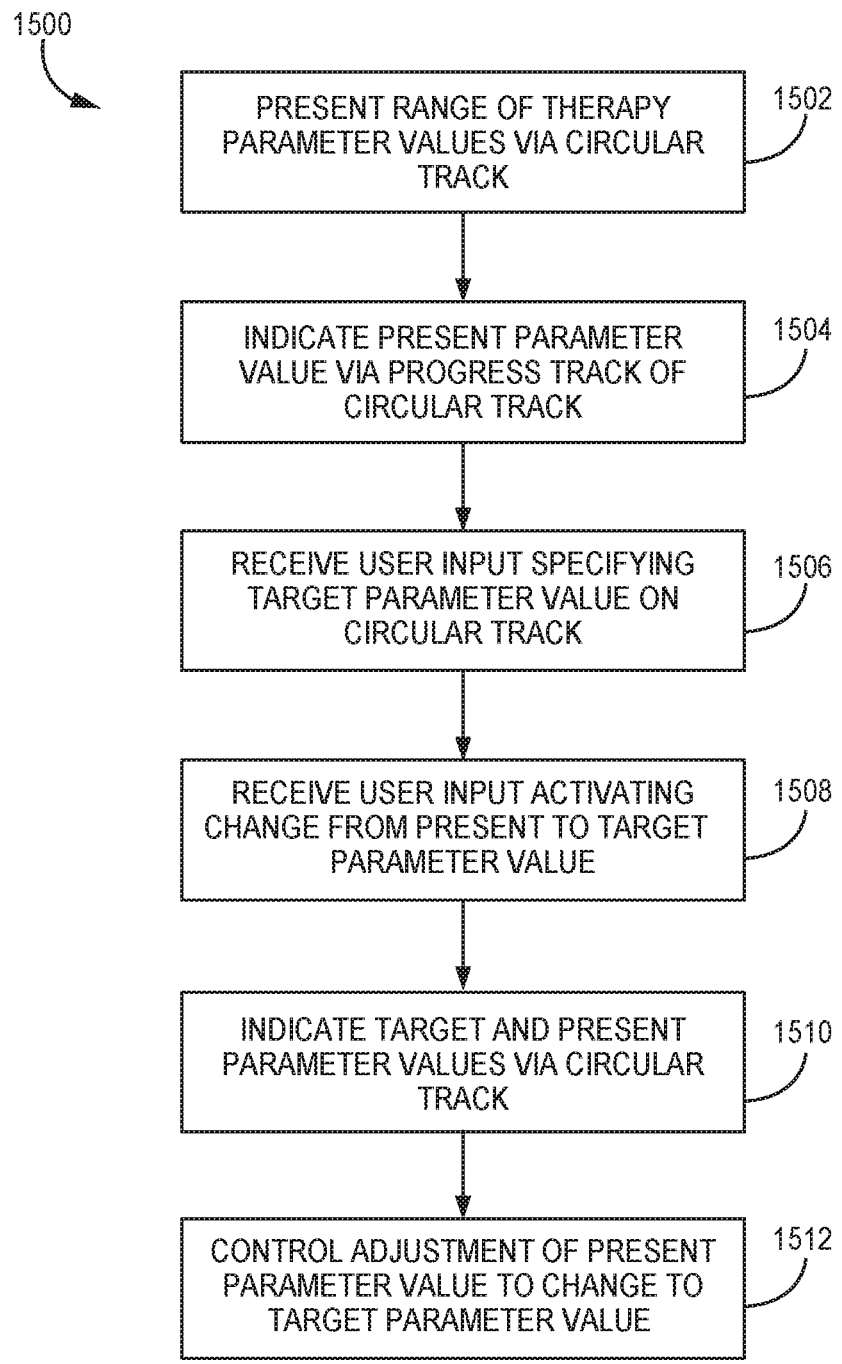
FIG. 15 is a flowchart illustrating an example process by which a computing device may perform one or more techniques of this disclosure.

FIG. 15 is a flowchart illustrating an example process 1500 by which a computing device may perform one or more techniques of this disclosure. Process 1500 may begin when the computing device presents a range of therapy parameter values via a circular track (1502). Examples of the circular track include circular track 404 of FIGS. 5A-5D, as well as outer ring 414 and inner ring 416 of FIG. 6. Additionally, the computing device may indicate a present parameter value (e.g., for the therapy parameter) via a progress track of the circular track (1504). Examples of the progress track include progress track 403 of FIGS. 5A-5D and 6.

The computing device may receive user input specifying a target parameter value (for the therapy parameter) on the circular track (1506). For instance, the computing device may receive a user input that corresponds to changing the position of knob 402 along the circumference of circular track 404 or outer ring 414. Additionally, the computing device may receive user input activating a change of the therapy parameter from the present value to the target parameter value (1508). For instance, the user (e.g., a clinician) may activate the change of the parameter value once the clinician decides on the target parameter value and feeds in the target parameter value by moving knob 402. Systems of this disclosure may provide the activation step (1508) as a safeguard against erroneous target parameter values, in that the clinician has the opportunity to change the target parameter value before effecting any change in therapy parameters with which to treat a patient. Upon receiving the activation input, the computing device may adjust the therapy parameter to transition or change from the present parameter value to the target parameter value (1510). In various examples, the change may be instantaneous, or may be in the form of ramping. In an example of ramping, the computing device may gradually transition the therapy parameter value from the present value towards the target value.

According to some examples, this disclosure is directed to a method for adjusting a therapy parameter for a medical device. The method includes presenting, by a computing device a range of available parameter values for the therapy parameter via a circular track, indicating, by the computing device, a present parameter value for the therapy parameter via the circular track, and receiving, by the computing device, via a user interface (UI), user input specifying a target parameter value for the therapy parameter. The method further includes indicating, by the computing device, the target parameter value in conjunction with the present parameter value via the circular track, receiving by the computing device, via the UI, user input activating an adjustment from the present parameter value to the target parameter value, and in response to receiving the user input activating the adjustment, controlling, by the computing device, the medical device to adjust the therapy parameter value from the present parameter value to the target parameter value.

In some examples, adjusting the therapy parameter to change from the present parameter value to the target parameter value includes adjusting the therapy parameter in predetermined increments. According to some examples, the method further includes presenting, by the computing device, one or more markers corresponding to the predetermined increments via the circular track. In some examples, controlling the medical device to adjust the therapy parameter to change from the present parameter value to the target parameter value includes toggling the therapy parameter between two states. In some examples, the method further includes indicating, by the computing device, a current status of the change from the present parameter value to the target parameter value via the circular track.

According to some examples, the circular track includes an outer ring indicating the target parameter value and an inner ring indicating the present parameter value. In some examples, the circular track includes representations of the present parameter value and the target parameter value on a single ring. In some examples, the method further includes presenting, by the computing device, with the circular track, via the UI, at least one of a numerical value of the target parameter value, or a numerical value of the present parameter value. According to some examples, the therapy parameter includes one or more of an electrical stimulation parameter, a drug delivery parameter, or a postural parameter.

In some examples, the method further includes controlling, by the computing device, the medical device to deliver therapy configured according to the change from the present parameter value to the target parameter value. According to some examples, receiving the user input specifying the target parameter value for the therapy parameter includes receiving, by the computing device, user input positioning a UI element along the circular track. According to some examples, the user input positioning the UI element along the circular track includes one or more of a drag gesture that moves the UI element to an updated position, or a click gesture on a target position of the circular track. According to some examples, receiving the user input specifying the target parameter value for the therapy parameter includes receiving, by the computing device, one or more of a voice command indicating the target parameter value, or a touch-based gesture at a portion of the UI that is external to the circular track.

According to some examples, this disclosure is directed to a programming device for a medical device. The programming device includes a communication module configured to communicate with the medical device, a memory, a user interface (UI) configured to receive inputs and to output data via a circular track, and one or more processors. The processor(s) of the programming device are configured to present a range of available parameter values for the therapy parameter via a circular track, to indicate a present parameter value for the therapy parameter via the circular track, and to receive, via the UI, user input specifying a target parameter value for the therapy parameter. The processor(s) of the programming device are further configured to indicate the target parameter value in conjunction with the present parameter value via the circular track, to receive, via the UI, user input activating an adjustment from the present parameter value to the target parameter value and to control, in response to receiving the user input activating the adjustment, the medical device to adjust the therapy parameter value from the present parameter value to the target parameter value.

In some examples, this disclosure is directed to a system. The system includes a medical device and a programming device configured to communicate with the medical device. The programming device comprising one or more processors. The one or more processors of the programming device are configured to present a range of available parameter values for the therapy parameter via a circular track, to indicate a present parameter value for the therapy parameter via the circular track, and to receive, via a user interface (UI), user input specifying a target parameter value for the therapy parameter. The processor(s) of the programming device are further configured to indicate the target parameter value in conjunction with the present parameter value via the circular track, to receive, via the UI, user input activating an adjustment from the present parameter value to the target parameter value, and to control, in response to receiving the user input activating the adjustment, control the medical device to adjust the therapy parameter value from the present parameter value to the target parameter value.

According to some examples, to adjust the therapy parameter to change from the present parameter value to the target parameter value, the processor(s) of the programming device are configured to adjust the therapy parameter in predetermined increments. In some examples, the processor(s) of the programming device are further configured to present one or more markers corresponding to the predetermined increments via the circular track. According to some examples, to adjust the therapy parameter to change from the present parameter value to the target parameter value, the processor(s) of the programming device are configured to toggle the therapy parameter between two states. According to some examples, the processor(s) of the programming device are further configured to indicate a current status of the change from the present parameter value to the target parameter value via the circular track.

In some examples, the circular track comprises an outer ring indicating the target parameter value and an inner ring indicating the present parameter value. In some examples, the circular track includes representations of the present parameter value and the target parameter value on a single ring. According to some examples, the processor(s) of the programming device are further configured to present, with the circular track, via the UI, at least one of a numerical value of the target parameter value, or a numerical value of the present parameter value. In some examples, the therapy parameter comprises one or more of an electrical stimulation parameter, a drug delivery parameter, or a postural parameter.

According to some examples, the processor(s) of the programming device are further configured to control the medical device to deliver therapy configured according to the change from the present parameter value to the target parameter value. In some examples, to receive the user input specifying the target parameter value for the therapy parameter, the one or processors are configured to receive user input positioning a UI element along the circular track. According to some examples, the user input positioning the UI element along the circular track comprises one or more of a drag gesture that moves the UI element to an updated position, or a click gesture on a target position of the circular track. In some examples, to receive the user input specifying the target parameter value for the therapy parameter, the processor(s) of the programming device are configured to receive one or more of a voice command indicating the target parameter value, or a touch-based gesture at a portion of the UI that is external to the circular track. In various examples, this disclosure is directed to a method for adjusting a therapy parameter value for a medical device. The method includes presenting a range of parameter values on a circular track, indicating a present parameter value on the circular track, and receiving user input specifying a target parameter value on the circular track. The method may further include receiving user input activating an adjustment from the present parameter value to the target parameter value, and in response to the user input, adjusting the therapy parameter value to change from the present parameter value to the target parameter value.

In some implementations of the method, adjusting the therapy parameter value to change from the present parameter value to the target parameter value includes adjusting the therapy parameter in predetermined increments. According to some implementations of the method, adjusting the therapy parameter value to change from the present parameter value to the target parameter value includes toggling the therapy parameter between two states. In some implementations of the method, adjusting the therapy parameter value to change from the present parameter value to the target parameter value includes adjusting the therapy parameter in predetermined increments.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A method for adjusting a therapy parameter for a medical device, the method comprising:
presenting, by a computing device, a range of available parameter values for the therapy parameter via a circular track;
presenting, by the computing device, on the circular track, a visual indication of a numeric value representing a present parameter value for the therapy parameter;
receiving, by the computing device, via a user interface (UI), user input specifying a target parameter value for the therapy parameter, wherein the target parameter value is either higher than the present parameter value or lower than the present parameter value;

presenting, by the computing device, on the circular track, a visual indication of a numeric value representing the target parameter value in conjunction with the visual indication of the numeric value representing the present parameter value;

receiving by the computing device, via the UI, user input activating an adjustment from the present parameter value to the target parameter value; and in response to receiving the user input activating the adjustment, controlling, by the computing device, the medical device to adjust the therapy parameter value by performing one of:

increasing the therapy parameter value from the present parameter value to the target parameter value based on the target parameter value being higher than the present parameter value, or decreasing the therapy parameter value from the present parameter value to the target parameter value based on the target parameter value being lower than the present parameter value.

2. The method of claim 1, wherein adjusting the therapy parameter to change from the present parameter value to the target parameter value comprises adjusting the therapy parameter in predetermined increments until the therapy parameter value reaches the target parameter value.

3. The method of claim 2, further comprising presenting, by the computing device, one or more markers corresponding to the predetermined increments via the circular track.

4. The method of claim 1, wherein controlling the medical device to adjust the therapy parameter to change from the present parameter value to the target parameter value comprises toggling the therapy parameter between the present parameter value and the target parameter value.

5. The method of claim 1, further comprising indicating, by the computing device, via the circular track, a current adjustment status of the therapy parameter value from the present parameter value to the target parameter value.

6. The method of claim 1, wherein the circular track comprises an outer ring including the visual indication of the numeric value representing the target parameter value and an inner ring including the visual indication of the numeric value representing the present parameter value.

7. The method of claim 1, wherein the circular track includes the visual indication of the numeric value representing the present parameter value and the visual indication of the numeric value representing the target parameter value on a single ring.

8. The method of claim 1, wherein the therapy parameter comprises one or more of:
an electrical stimulation parameter,
a drug delivery parameter, or
a postural parameter.

9. The method of claim 1, further comprising controlling, by the computing device, the medical device to deliver therapy configured according to the therapy parameter value being adjusted from the present parameter value to the target parameter value.

10. The method of claim 1, wherein receiving the user input specifying the target parameter value for the therapy parameter comprises receiving, by the computing device, user input positioning a UI element along the circular track.

11. The method of claim 10, wherein the user input positioning the UI element along the circular track comprises one or more of:

a drag gesture that moves the UI element to an updated position, or
a click gesture on a target position of the circular track.

12. The method of claim 1, wherein receiving the user input specifying the target parameter value for the therapy parameter comprises receiving, by the computing device, one or more of:
a voice command indicating the target parameter value, or
a touch-based gesture at a portion of the UI that is external to the circular track.

13. A programming device for a medical device comprising:
a communication module configured to communicate with the medical device;
a memory;
a user interface (UI) configured to receive inputs and to output data via a circular track; and
one or more processors configured to:
present a range of available parameter values for the therapy parameter via the circular track;
present, on the circular track a visual indication of a numeric value representing a present parameter value for the therapy parameter;
receive, via the UI, user input specifying a target parameter value for the therapy parameter
present, on the circular track, a visual indication of a numeric value representing the target parameter value in conjunction with the visual indication of the numeric value representing the present parameter value;
receive, via the UI, user input activating an adjustment from the present parameter value to the target parameter value, wherein the target parameter value is either higher than the present parameter value or lower than the present parameter value; and
in response to receiving the user input activating the adjustment, control the medical device to adjust the therapy parameter value from the present parameter value to the target parameter value, wherein to adjust the therapy parameter value, the one or more processors are configured to at least one of:
increase the therapy parameter value from the present parameter value to the target parameter value based on the target parameter value being higher than the present parameter value; or
decrease the therapy parameter value from the present parameter value to the target parameter value based on the target parameter value being lower than the present parameter value.

14. The programming device of claim 13, wherein to adjust the therapy parameter to change from the present parameter value to the target parameter value, the one or more processors are configured to adjust the therapy parameter in predetermined increments until the therapy parameter value reaches the target parameter value.

15. The programming device of claim 14, wherein the one or more processors are further configured to present one or more markers corresponding to the predetermined increments via the circular track.

16. The programming device of claim 13, wherein to adjust the therapy parameter to change from the present parameter value to the target parameter value, the one or more processors are configured to toggle the therapy parameter between the present parameter value and the target parameter value.

17. The programming device of claim 13, wherein the one or more processors are further configured to indicate, via the circular track, a current adjustment status of the therapy parameter value from the present parameter value to the target parameter value.

18. The programming device of claim 13, wherein the circular track comprises an outer ring including the visual indication of the numeric value representing the target parameter value and an inner ring including the visual indication of the numeric value representing the present parameter value.

19. The programming device of claim 13, wherein the circular track includes the visual indication of the numeric value representing the present parameter value and the visual indication of the numeric value representing the target parameter value on a single ring.

20. The programming device of claim 13, wherein the therapy parameter comprises one or more of:
an electrical stimulation parameter,
a drug delivery parameter, or
a postural parameter.

21. The programming device of claim 13, wherein the one or more processors are further configured to control the medical device to deliver therapy configured according to the therapy parameter value being adjusted from the present parameter value to the target parameter value.

22. The programming device of claim 13, wherein to receive the user input specifying the target parameter value for the therapy parameter, the one or more processors are configured to receive user input positioning a UI element along the circular track.

23. The programming device of claim 22, wherein the user input positioning the UI element along the circular track comprises one or more of:
a drag gesture that moves the UI element to an updated position, or
a click gesture on a target position of the circular track.

24. The programming device of claim 13, wherein to receive the user input specifying the target parameter value for the therapy parameter, the one or more processors are configured to receive one or more of:
a voice command indicating the target parameter value, or
a touch-based gesture at a portion of the UI that is external to the circular track.

25. The programming device of claim 13, wherein the one or more processors are further configured to:
detect that the therapy parameter value has changed from the present parameter value to the target parameter value; and
based on the detection, output a notification indicating that the therapy parameter value has reached the target parameter value.

26. The programming device of claim 25, wherein to output the notification, the one or more processors are configured to control output of haptic feedback.

27. A system comprising:
a medical device;
a programming device configured to communicate with the medical device, the programming device comprising one or more processors configured to:
present a range of available parameter values for the therapy parameter via a circular track;
present, on the circular track, a visual indication of a numeric value representing a present parameter value for the therapy parameter;
receive, via a user interface (UI), user input specifying a target parameter value for the therapy parameter, wherein the target parameter value is either higher than the present parameter value or lower than the present parameter value;
present, on the circular track, a visual indication of a numeric value representing the target parameter value in conjunction with the visual indication of the numeric value representing the present parameter value;
receive, via the UI, user input activating an adjustment from the present parameter value to the target parameter value; and
in response to receiving the user input activating the adjustment, control the medical device to adjust the therapy parameter value from the present parameter value to the target parameter value, wherein to adjust the therapy parameter value, the one or more processors are configured to at least one of:
increase the therapy parameter value from the present parameter value to the target parameter value based on the target parameter value being higher than the present parameter value; or
decrease the therapy parameter value from the present parameter value to the target parameter value based on the target parameter value being lower than the present parameter value.

28. The system of claim 27, wherein the one or more processors of the programming device are further configured to indicate, via the circular track, a current adjustment status of the therapy parameter value from the present parameter value to the target parameter value.

29. The system of claim 27, wherein the circular track comprises an outer ring including the visual indication of the numeric value representing the target parameter value and an inner ring including the visual indication of the numeric value representing the present parameter value.

30. The system of claim 27, wherein the circular track includes the visual indication of the numeric value representing the present parameter value and the visual indication of the numeric value representing the target parameter value on a single ring.

* * * * *